United States Patent
Banet et al.

(10) Patent No.: US 8,239,010 B2
(45) Date of Patent: Aug. 7, 2012

(54) SYSTEM FOR MEASURING VITAL SIGNS DURING HEMODIALYSIS

(75) Inventors: Matt Banet, Kihei, HI (US); Andrew James King, Rancho Santa Fe, CA (US)

(73) Assignee: Sotera Wireless, Inc., San Diego, CA (US)

( * ) Notice: Subject to any disclaimer, the term of this patent is extended or adjusted under 35 U.S.C. 154(b) by 410 days.

(21) Appl. No.: 12/559,080

(22) Filed: Sep. 14, 2009

(65) Prior Publication Data

US 2011/0066006 A1   Mar. 17, 2011

(51) Int. Cl.
*A61M 1/14* (2006.01)
(52) U.S. Cl. ........ 600/513; 600/485; 600/504; 604/4.01
(58) Field of Classification Search .................. None
See application file for complete search history.

(56) References Cited

U.S. PATENT DOCUMENTS

| | | | |
|---|---|---|---|
| 2003/0130590 A1* | 7/2003 | Bui et al. | 600/537 |
| 2009/0222119 A1* | 9/2009 | Plahey et al. | 700/94 |
| 2010/0234786 A1* | 9/2010 | Fulkerson et al. | 604/4.01 |
| 2010/0241011 A1* | 9/2010 | Mccombie et al. | 600/485 |
| 2010/0312115 A1* | 12/2010 | Dentinger | 600/450 |

* cited by examiner

*Primary Examiner* — Kennedy Schaetzle
(74) *Attorney, Agent, or Firm* — Michael A. Whittaker; Acuity Law Group, P.C.

(57) ABSTRACT

The invention provides a system for continuously monitoring a patient during hemodialysis. The system includes a hemodialysis machine for performing the hemodialysis process that features a controller, a pump, a dialyzer filter, a lumen, and an interface to a body-worn monitor. A patient attaches to the dialysis machine through the lumen, and wears a body-worn monitor for continuously measuring blood pressure. The monitor includes an optical system for measuring an optical waveform, an electrical system for measuring an electrical waveform, and a processing component for determining a transit time between the optical and electrical waveforms and then calculating a blood pressure value from the transit time. The body-worn monitor features an interface (e.g. a wired serial interface, or a wireless interface) to transmit the blood pressure value to the controller within the hemodialysis machine. The controller is configured to receive the blood pressure value, analyze it, and in response adjust the dialysis process.

20 Claims, 15 Drawing Sheets

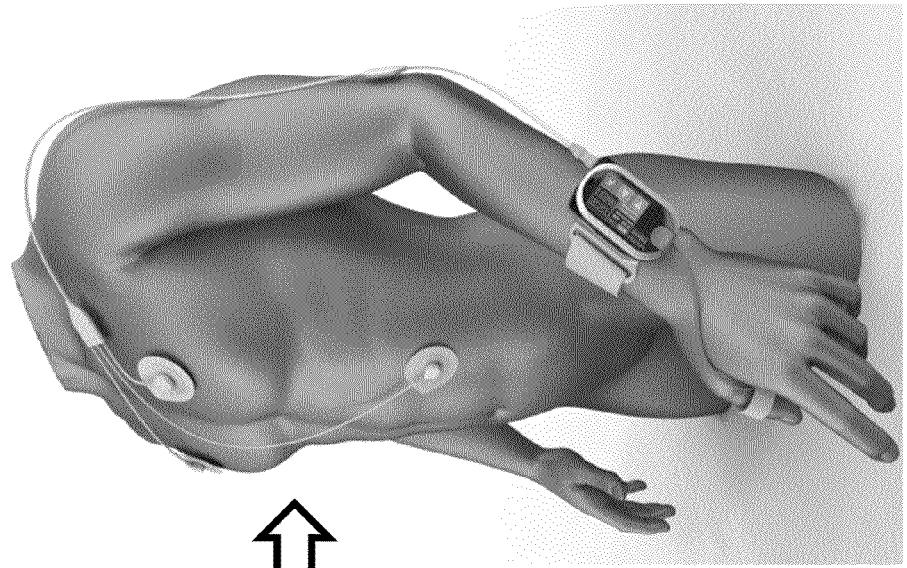
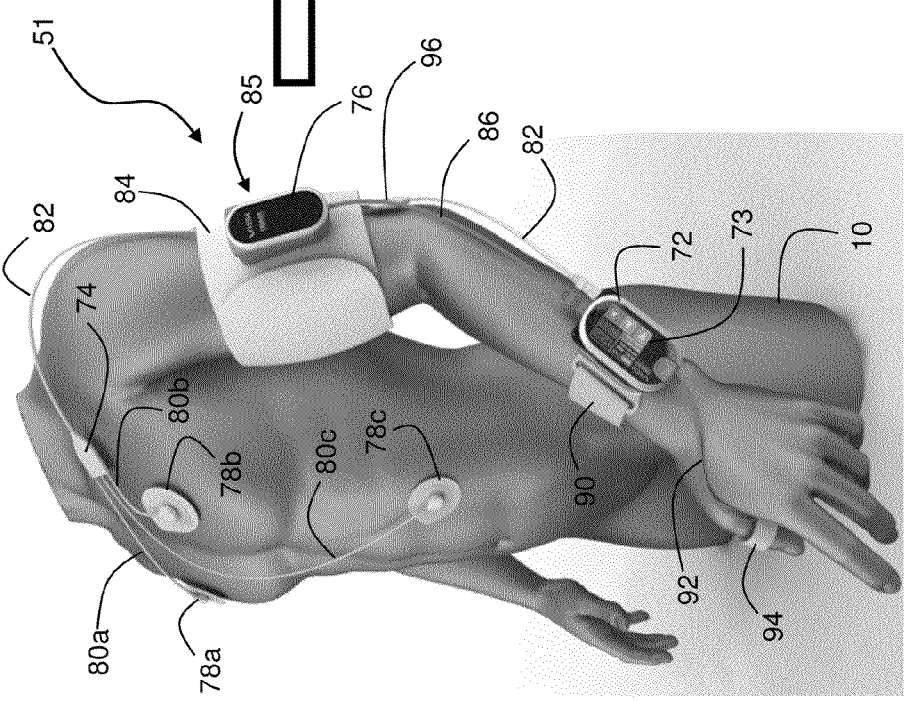

SYSTEM FOR MEASURING VITAL SIGNS DURING HEMODIALYSIS

CROSS REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention relates to systems for monitoring vital signs, and particularly blood pressure, during hemodialysis.

2. Description of the Related Art

Patients in late-stage renal failure typically require hemodialysis for survival. During a hemodialysis treatment, blood is extracted from a patient's veins to remove excess water and waste products, such as potassium and uric acid, with a process that combines diffusive clearance across a membrane (dialysis) and convective clearance (ultrafiltration). Rapid extraction of fluid can cause the patient's blood pressure to quickly decrease due to the lack of volume in the vessels. This can also increase or reduce the patient's heart rate, increase their body temperature, and induce nausea and severe fatigue. In some cases these side effects can be life-threatening. Frequent hypotensive episodes, for example, have been linked to increased mortality in the dialysis population.

A method known as pulse transit time (PTT) can continuously measure a patient's blood pressure with only intermittent calibration with a cuff-based system. PTT, defined as the transit time for a pressure pulse launched by a heartbeat in a patient's arterial system, has been shown in a number of studies to correlate to both systolic (SYS) and diastolic (DIA) blood pressure. In these studies, PTT is typically measured with a conventional vital signs monitor that includes separate modules to determine both an electrocardiogram (ECG) and pulse oximetry value (SpO2). During a typical PTT measurement, multiple electrodes attach to a patient's chest to determine a time-dependent ECG waveform characterized by a sharp spike called a 'QRS complex'. The QRS complex indicates an initial depolarization of ventricles within the heart and, informally, marks the beginning of a heartbeat and a pressure pulse that follows. Pulse oximetry is typically measured with a bandage or clothespin-shaped sensor that attaches to a patient's finger, and typically includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine the patient's blood oxygen saturation level and a time-dependent optical waveform called a photoplethysmograph (PPG). Time-dependent features of the optical waveform indicate both pulse rate and a volumetric absorbance change in an underlying artery (e.g., in the finger) caused by the propagating pressure pulse.

Typical PTT measurements determine the time separating a maximum point on the QRS complex (indicating the peak of ventricular depolarization) and a foot of the optical waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff. Typically during the calibration process the blood pressure cuff is applied to the patient and used to make one or more blood pressure measurements. Going forward, the calibration blood pressure measurements are used, along with a change in PTT, to determine the patient's blood pressure and blood pressure variability. PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and optical waveform, which are then processed to determine PTT.

SUMMARY OF THE INVENTION

This invention provides a body-worn monitor for continuously measuring a PTT-based blood pressure for patients undergoing hemodialysis. Blood pressure is determined with a technique referred to herein as the 'Composite Method' which relies on a series of optical, electrical, motion, and pressure sensors worn on the patient's body. A finger-worn sensor that includes the optical and electrical sensors is optimized for the hemodialysis process and attaches to one of the patient's fingers (preferably their thumb) to measure PTT and, ultimately, blood pressure.

Continuous measurements made using the Composite Method detect rapid changes in blood pressure that could otherwise be missed with conventional techniques, such as cuff-based oscillometry. The system for making the continuous measurements also includes a wireless interface that transmits information from the patient's hemodialysis machine (or directly from the patient) to a central monitoring station. This allows a single medical professional to monitor several patients simultaneously and efficiently detect events such as a rapid drop in blood pressure, or a sudden change in heart rate. When combined with the Composite Method, this system improves patient safety during hemodialysis. The invention additionally provides both manual and automated methods for interpreting changes in a patient's vital signs and, in response, adjusting settings on a hemodialysis machine. Further, the invention can facilitate development of personalized algorithms that can avoid hypotensive episodes, thereby increasing both the safety and comfort of hemodialysis.

The Composite Method (also referred to as the 'Hybrid Method' in the patent applications referenced herein) features both pressure-dependent and pressure-free measurements. These are described in detail is the following patent applications, the contents of which are fully incorporated herein by reference: 1) DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); 2) VITAL SIGN MONITOR MEASURING BLOOD PRESSURE USING OPTICAL, ELECTRICAL, AND PRESSURE WAVEFORMS (U.S. Ser. No. 12/138,194; filed Jun. 12, 2008); and, 3) VITAL SIGN MONITOR FOR CUFFLESSLY MEASURING BLOOD PRESSURE CORRECTED FOR VASCULAR INDEX (U.S. Ser. No. 12/138,199; filed Jun. 12, 2008).

Algorithms for addressing patient motion during the Composite Method are described in the following patent applications, the contents of which are fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009).

During the Composite Method, a pressure-dependent 'indexing' measurement, typically made once every 4-8 hours with a removable cuff-based system, determines SYS, DIA, and mean arterial (MAP) pressures using a derivative of oscillometry that takes place during inflation. The indexing measurement is based on the discovery that PTT is strongly modulated by an applied pressure, and uses this relationship to determine a patient-specific slope relating blood pressure and PTT. Specifically, pressure applied during an indexing measurement gradually decreases the patient's blood flow and consequent blood pressure, and therefore increases PTT. A mathematical model relates the applied pressure to an 'effective MAP' representing an estimated mean arterial pressure in the patient's arm. Using this model, paired data points featuring values for PTT and effective MAP are determined for each heartbeat during the indexing measurement. The pairs of PTT/effective MAP readings can be fit with a linear model to determine a patient-specific slope relating PTT to blood pressure. Going forward, a medical professional removes the cuff-based system used to perform the indexing measurement, and the system makes continuous blood pressure measurements (cNIBP) based on PTT to characterize the patient.

For the pressure-dependent measurement, an armband featured in the body-worn monitor includes a small mechanical pump that inflates a bladder to apply pressure to an underlying artery according to a pressure waveform. The armband is typically located on the patient's upper arm, proximal to the brachial artery, and time-dependent pressure is measured by an internal pressure sensor (e.g. an in-line Wheatstone bridge or strain gauge). The pressure waveform gradually ramps up in a mostly linear manner during inflation, and then deflates through a 'bleeder valve' during deflation. During inflation, mechanical pulsations corresponding to the patient's heartbeats couple into the bladder as the applied pressure approaches DIA. The mechanical pulsations modulate the pressure waveform so that it includes a series of time-dependent oscillations. The oscillations are processed according to the Composite Method to determine MAP, SYS, and DIA.

Pressure-free cNIBP measurements immediately follow the pressure-dependent measurements, and are typically made by determining PTT with the same optical and electrical sensors used in the pressure-dependent measurements. Specifically, using the Composite Method, the body-worn monitor continuously determines SYS and DIA by processing PTT, a calibration describing the relationship between PTT and blood pressure, and in some cases other properties of the PPG (relating, e.g., to the shape of the PPG waveform), along with the measurements of SYS, DIA, and MAP made during the pressure-dependent measurement.

In addition to blood pressure, the body-worn monitor measures heart rate and respiratory rate from components of the electrical waveform, and SpO2 from optical waveforms generated with both red and infrared radiation. Methods for simultaneously calculating SpO2 and cNIBP using the Composite Method are described, for example, in the following patent application, the contents of which are incorporated herein by reference: BODY-WORN PULSE OXIMETER (U.S. Ser. No. 61/218,062; filed Jun. 17, 2009). The body-worn monitor can also measure temperature and patient motion with additional sensors (e.g. a thermocouple and one or more accelerometers).

In one aspect, the invention provides a system for characterizing a patient undergoing a hemodialysis process. The system includes a hemodialysis machine featuring an interface that continuously receives a blood pressure value (e.g., receives a blood pressure at least every minute, and in some cases every second), a processor unit that processes the blood pressure value, and a display unit that displays the blood pressure value. A body-worn monitor interfaces to the hemodialysis machine. This monitor includes a finger-worn sensor (based, e.g., on a flexible patch or an annular finger ring) with an embedded light source and photodetector. Collectively these optics measure an optical waveform from the patient. To measure an electrical waveform, the body-worn monitor includes first and second electrodes that measure, respectively, first and second electrical signals from the patient (using, e.g., chest-worn electrodes), and an electrical circuit that receives and amplifies these signals.

The monitor additionally includes a cuff-based system featuring an inflatable bladder, a pump, and a pressure sensor. During a measurement, the cuff-based system activates the pump to inflate the bladder. The pressure sensor then measures pressure in the bladder to generate a pressure waveform. A processing module within the monitor processes: i) the optical waveform and the electrical waveform to determine a set of time differences between features in these waveforms when the pump is inflating the bladder; ii) the set of time differences and the pressure waveform to determine a blood pressure calibration; and iii) the blood pressure calibration and a time difference between the optical and electrical waveforms when the pump is not inflating the bladder to determine a blood pressure value. Once the blood pressure value is determined, a transmission system continuously transmits it to both the hemodialysis machine and a central station. In embodiments, a heart rate determined from the electrical waveform is transmitted to these systems as well.

In embodiments, the finger-worn sensor includes the first electrode. This simplifies and expedites application of the monitor to the patient. Typically the electrode is a conductive metal electrode that is not disposable. In other embodiments the cuff-based system includes a second processing module configured to process the pressure waveform to determine values for SYS, DIA, and MAP. Here, the cuff-based system includes a cable that plugs into the processing module within the body-worn monitor to supply the pressure waveform and blood pressure values.

In other embodiments, the transmission system features a wireless system (based, e.g., on 802.15.4 or 802.11) that wirelessly transmits the blood pressure value and ECG waveform to both the hemodialysis machine and central station. The central station can include an interface that receives and displays blood pressure values, heart rate values, and ECG waveforms from a plurality of patients undergoing hemodialysis. For example, the central station can be a computer with a large, flat-panel monitor that is easily viewable throughout the dialysis clinic. In this embodiment the interface typically includes a field indicating the patient from which these data originated. The central station can include an alarm system for entering a blood pressure threshold for each patient. During operation, the alarm system generates an alarm for a patient when a blood pressure value or heart rate exceeds a threshold value.

In still other embodiments, the processing unit within the hemodialysis machine is configured to adjust the hemodialysis process after processing the blood pressure or heart rate value. This adjustment, for example, depends on the magnitude of these values. It can be implemented in a 'closed loop' manner so that the hemodialysis process can be continually updated and improved for a given patient.

In another aspect, the invention features a body-worn monitor, attached to the patient and configured to interface to a hemodialysis machine, which includes the above-described systems for measuring blood pressure and heart rate. The monitor features a first transmission system for transmitting blood pressure values to the hemodialysis machine when the patient is connected to the hemodialysis machine, and a second transmission system for transmitting information to a remote receiver when the patient is disconnected from the hemodialysis machine. In embodiments, both the first and second transmission systems feature wireless systems, and the remote receiver is a computer (e.g. a computer connected to the Internet or a remote call center).

In embodiments the body-worn monitor includes one or more input ports. One of the import ports, for example, can be configured to connect to the second transmission system, while the other can be configured to attach to the sensor that includes the optical system. In this way, when the patient leaves the hemodialysis clinic, the sensor can be removed so that the monitor is relatively unobtrusive, connects only to body-worn electrodes, and only measures properties derived from the patient's ECG waveform. The second transmission system can then be plugged into another input port and activated. In other embodiments, the vital sign monitor includes a user interface that allows a medical professional or patient to activate either the first or second transmission systems.

The two transmission systems can each be part of a common transmission system. Such a system, for example, may be a single wireless system. In this case, the first transmission system includes compiled computer code that instructs it to transmit blood pressure values to the hemodialysis machine, and the second transmission system includes compiled computer code that instructs it to transmit information to the remote receiver. Alternatively the two transmission systems can be separate wireless systems (e.g. systems operating 802.11 and/or 802.15.4 protocols) or wired systems (e.g. Ethernet-based systems). Information transmitted by the second transmission system, for example, can describe blood pressure, heart rate, and/or cardiac parameters describing a high heart rate, low heart rate, bradycardia, bradytachycardia, asystole, ventricular fibrillation, ventricular tachycardia, apnea, and heart rate variability. The information can also be a time-dependent waveform, such as an ECG waveform, or an alarm determined from either the waveform or cardiac parameters.

BRIEF DESCRIPTION OF THE DRAWINGS

FIGS. 10A and 10B show an image of a body-worn monitor of the invention attached to a hemodialysis patient with and without, respectively, a cuff-based pneumatic system used for an indexing measurement;

DETAILED DESCRIPTION OF THE INVENTION

Figure 1:
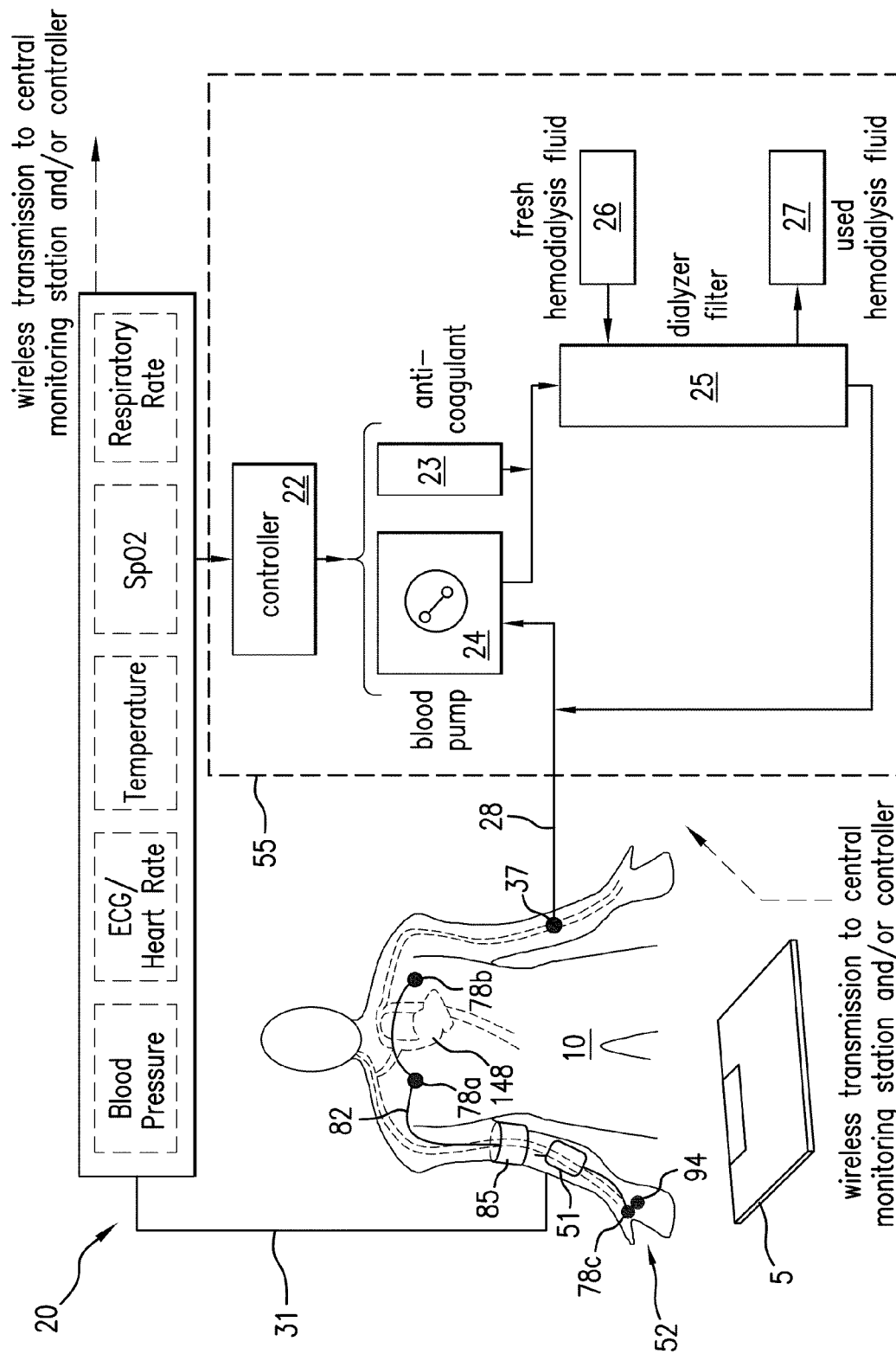
FIG. 1 shows a schematic drawing of a system according to the invention used to monitor a patient during a hemodialysis process.

FIG. 1 shows a schematic drawing of a system 20 for continuously monitoring vital signs, and particularly blood pressure, from a patient 10 attached to a hemodialysis machine 55. The system 20 features a body-worn monitor 51 that uses the Composite Method to measure SYS, DIA and other vital signs (e.g. heart rate, temperature, SpO2, and respiratory rate) and time-dependent waveforms (e.g. ECG, PPG). The body-worn monitor 51 connects to a cuff-based monitor 85 featuring an embedded, inflatable bladder that connects to a cuff-based pneumatic system (described below). During an indexing measurement the cuff-based monitor 85 attaches proximal to the patient's brachial artery. The body-worn monitor 51 additionally connects to a finger-worn sensor 94 featuring a cable terminated with an end portion 52 that typically wraps around the base of the patient's thumb. The end portion 52 includes one or more electrodes 78c and an optical sensor, typically with multiple light-emitting diodes and a photodetector. A cable 82 connects the body-worn monitor 51 to a primary electrode 78a and reference electrode 78b typically adhered to the patient's chest. During a hemodialysis process, the body-worn monitor 51 performs an indexing measurement using the optical sensor within the finger-worn sensor 94, electrodes 78a, 78b, and 78c, and cuff-based system 85. Collectively these systems measure, respectively, PPG, ECG, and pressure waveforms. A microprocessor in the body-worn monitor 51 receives these waveforms and then processes them according to the Composite Method, described in detail below, to continuously determine the patient's blood pressure and other vital signs. This information transfers through a cable 31 to a controller 22 within the hemodialysis machine 55 and sent wirelessly to a receiver in central monitoring station. Alternatively, the cable 31 can be replaced by a wireless interface, such as a Bluetooth (802.15.4) or WiFi (802.11) interface. In this case, the body-worn monitor 51 includes the controller, and all measurements are made on the patient's body and sent wirelessly to the hemodialysis machine 55.

Figure 4:
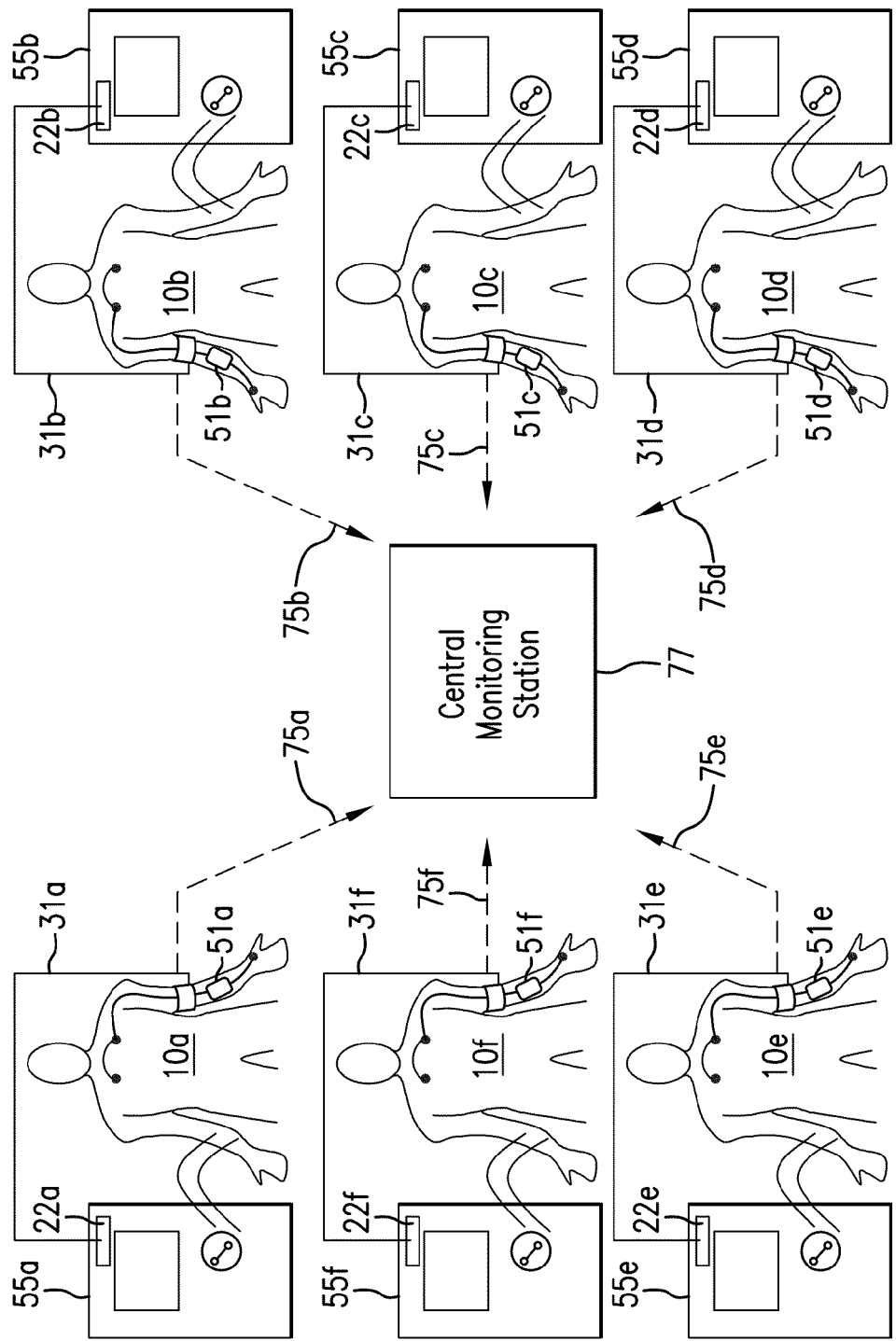
FIG. 4 shows a schematic drawing of multiple hemodialysis patients, each monitored with a system of FIG. 1 that wirelessly transmits information to a central monitoring station.

The central monitoring station, shown schematically in FIG. 4, is typically centrally located in a hemodialysis clinic. It typically includes a computer and large flat-panel monitor that display vital signs, waveforms, weight, and information concerning the hemodialysis process from each patient.

In typical applications, the Composite Method determines blood pressure over short time intervals that range from approximately 40 seconds to the time required for a single heartbeat (e.g. 1 second). A 'rolling average' may be deployed if measurements are displayed with high frequency. This allows both a medical professional and the controller 22 within the hemodialysis machine 55 to detect rapid changes in the patient's physiological condition which can occur during the hemodialysis process, and are too fast to be monitored with conventional means, e.g. a standard blood pressure cuff. Standard cuff measurements currently occur every 30 minutes, an interval based largely on patient tolerability.

Rapid changes in a patient's hemodynamics can occur, for example, if blood is extracted and filtered at a non-optimal rate. They include a rapid change in blood pressure (e.g. hypotension, hypertension), fatigue, nausea, chest pain, extreme changes in body temperature, high and low heart rate, and low SpO2. These conditions may necessitate rapid modifications in the hemodialysis process that, once completed, can improve the safety of the patient.

Other systems for monitoring vital signs may be used with the system shown in FIG. 1. For example, to measure SpO2, the optical sensor 52 can include optics (e.g. LEDs operating near 600 and 900 nm) normally found within a pulse oximeter, and the electrodes 78a, 78b can include a thermocouple to measure the patient's core body temperature. The ECG system may also include systems for measuring respiratory rate using techniques such as impedance pneumography. Here, a low-amperage current modulated at a high frequency passes from one electrode to another, and is further modulated by breathing-induced capacitance changes in the patient's chest. The resultant signal can be processed to determine respiratory rate. Additionally, the body-worn monitor 51 can include software that detects diagnostic cardiac properties such as heart rate variability, arrhythmias, ventricular tachycardia, and atrial fibrillation. The body-worn monitor can include one or more accelerometers to measure and account for patient motion, as described in the above-referenced patent applications.

Weight is an important parameter for characterizing hemodialysis, as it indicates the amount of fluid removed from the patient 10 by the dialysis machine 55. It is therefore typically measured before and after hemodialysis. The system 20 can thus include a wireless weight scale 5 that, during operation, transmits the patient's weight to both the controller 22 within the hemodialysis machine 55, and to the central monitoring station. In embodiments, the weight scale 5 is embedded directly in a chair, proximal to the hemodialysis machine 55 and used to support the patient. This allows, for example, real-time determination of the patient's weight during the hemodialysis process. In this case, weight information is wirelessly transmitted using either a Bluetooth (802.15.4) or WiFi (802.11) interface to the central monitoring station.

During the hemodialysis process, the patient 10 is connected to a blood pump 24 within the hemodialysis machine 55 through an arteriovenous fistula into which a catheter 37 is inserted. The catheter 37 plunges into a large vein (typically a brachial vein), and further connects to a lumen 28 for fluid extraction. Once hemodialysis begins, the controller 22 initiates the blood pump 24 and regulates the following: i) the rate at which the patient's blood is withdrawn; ii) the blood flow rate through the dialysis membrane; iii) the passage of fluid across a semi-permeable membrane in the dialyzer filter 25 (i.e. the ultrafiltration rate); and iv) the flow and composition of the dialysate on the opposite side of the membrane. These processes remove toxins (e.g. uric acid, free water, potassium, phosphate, and other waste products) from the patient's blood that would normally be removed by the kidneys. As blood is introduced from the patient to the dialyzer filter 25, an anti-coagulant 23 is combined into the fluid to ensure that blood does not coagulate. Fresh dialysate 26 flows in a countercurrent fashion into the dialysis cartridge on the other side of the semi-permeable membrane. This creates a trans-membrane pressure gradient, causing free water and some dissolved solutes to move across the membrane according to a process termed 'convective clearance'. Convective clearance is combined with diffusive clearance whereby solutes traverse from the blood compartment into the dialysate (or vice versa) based on concentration differences and the reflective coefficient of the dialysis membrane. Total clearance equals the sum of diffusive and convective clearances. The dialysate is discarded and the cleansed blood exiting the dialysis cartridge is returned to the patient.

Figure 2:
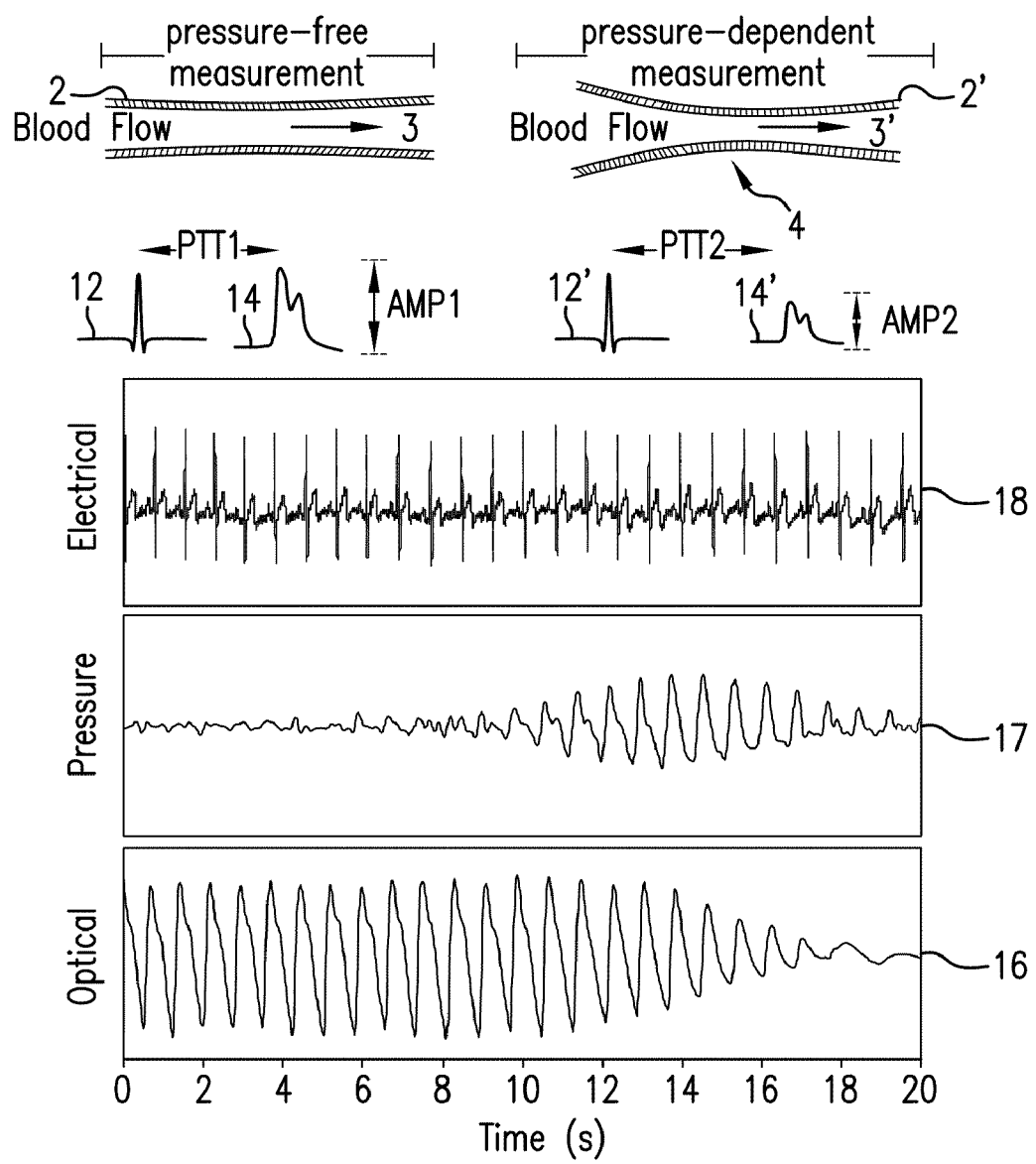
FIG. 2 shows graphs of time-dependent PPG, ECG, and pressure waveforms measured during pressure-free and pressure-dependent measurements of the Composite Method.

FIG. 2 illustrates the pressure-free and pressure-dependent measurements used in the Composite Method to continuously measure blood pressure for a patient undergoing a hemodialysis process. Working in concert, these measurements accurately and continuously determine the patient's blood pressure for an extended time without requiring an external calibration device. The Composite Method and the sensors it requires are described in detail in the above-referenced patent applications, the contents of which have been already incorporated herein by reference.

The cuff-based system includes an air bladder which, when pressurized with a mechanical pump, applies a pressure to an underlying artery (e.g. the brachial artery). An electrical system featuring a series of electrodes coupled to an amplifier/filter circuit within the body-worn monitor measures an ECG 12, 12' from the patient. The ECG 12, 12' features a conventional 'QRS' complex. The primary and reference electrodes are typically required to detect the necessary signals to generate an ECG 12, 12' with an adequate signal-to-noise ratio. At the same time, an optical system featuring a light source and photodiode measures a PPG 14, 14' featuring a series of 'pulses', each characterized by an amplitude of $AMP_{1/2}$ of a volumetric change in the patient's underlying artery. A preferred measurement site is above arteries in the patient's thumb. A microprocessor and analog-to-digital converter within the body-worn monitor detect and analyze the ECG 12, 12' and PPG 14, 14' waveforms to determine both $PTT_1$ (from the pressure-free measurement) and $PTT_2$ (from the pressure-dependent measurement). Typically the microprocessor determines both $PTT_1$ and $PTT_2$ by calculating the time difference between the peak of the QRS complex in the ECG 12, 12' and the foot (i.e. onset) of the PPG 14, 14'.

Applied pressure (indicated by the arrow 4) during the pressure-dependent measurement affects blood flow (indicated by arrows 3, 3') in the underlying artery 2, 2'. Specifically, the applied pressure has no affect on either $PTT_2$ or $AMP_2$ when it is less than DIA. When the applied pressure 4 reaches DIA it begins to compress the artery, thus reducing blood flow and the effective internal pressure. This causes $PTT_2$ to systematically increase relative to $PTT_1$, and $AMP_2$ to systematically decrease relative to $AMP_1$. $PTT_2$ increases and $AMP_2$ decreases (typically in a linear manner) as the applied pressure approaches the SYS within the artery 2, 2'. When the applied pressure reaches SYS, $AMP_2$ is completely eliminated and $PTT_2$ consequently becomes immeasurable. As described above, the pressure-dependent increase in $PTT_2$ is processed with a mathematical model to determine a patient-specific slope relating PTT and blood pressure; this is used for cNIBP measurements. The systematic decrease in the PPG's amplitude between $AMP_1$ and $AMP_2$ can be used to accurately determine SYS, as described in the above-referenced patent application describing the Composite Method. Such a measurement, for example, can be used in place of inflation-based oscillometry to determine SYS.

Typically during the Composite Method electrodes attach to the patient's thumb and chest in a configuration that resembles a conventional 'Einthoven's triangle' configuration. This ultimately yields three unique ECG waveforms, each corresponding to a separate vector; any of these can be used for the cNIBP measurement. Within the body-worn monitor, the signals are processed using the amplifier/filter circuit to determine an analog electrical signal, which is digitized with an analog-to-digital converter to form a digital ECG, which can then be stored in memory and processed. The optical sensor typically includes an optical module featuring an integrated photodetector, amplifier, and pair of light sources. The light sources typically operate in the infrared, near 900 nm. The optical sensor detects reflected radiation, which is further processed with a second amplifier/filter circuit within the body-worn monitor. This results in a PPG, which, as described above, includes a series of pulses, each corresponding to an individual heartbeat. A second optical sensor can also be used to measure a second optical waveform from one of these arteries.

Figure 3:
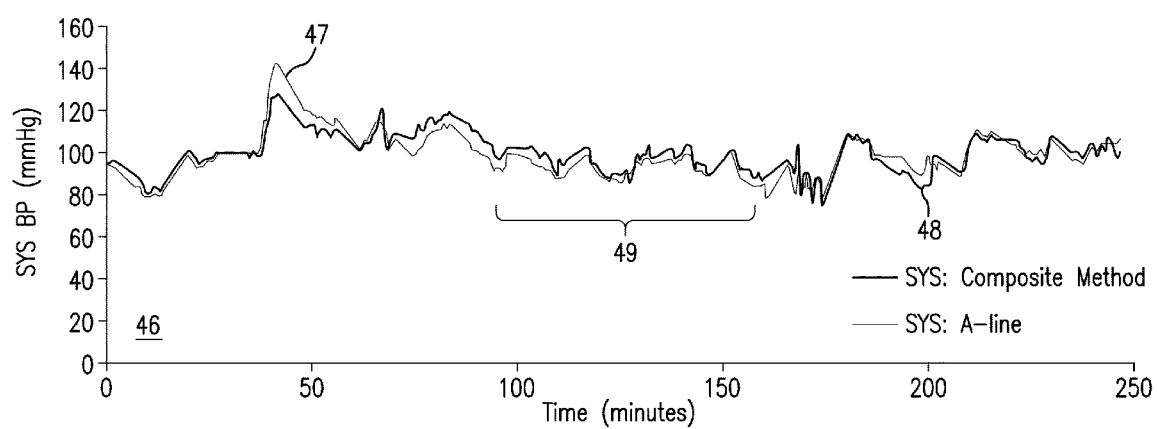
FIG. 3 shows a graph of SYS measured using an A-line (gray trace) and the Composite Method (black trace) from a patient undergoing a hemodialysis process.

FIG. 3 shows data indicating the efficacy of the Composite Method for measuring blood pressure from a patient undergoing a hemodialysis process. The figure shows time-dependent SYS measured from the patient using a body-worn monitor and the Composite Method (48; black line) compared to that measured with an A-line inserted in the patient's femoral artery (47; gray line). The A-line, particularly the femoral A-line, is often considered to be a 'gold standard' for measuring blood pressure. To generate these data, simultaneous measurements were continuously made over a 4-hour period, averaged over consecutive 40-second periods, and then plotted as a function of time. A single cuff-based indexing measurement, which took about 40 seconds, was performed at the beginning of the 4-hour period. All subsequent measurements were pressure-free cNIBP measurements. As is clear from the data, blood pressure measured with the Composite Method accurately tracks that made by the A-line, even during periods of extreme volatility, as indicated by bracket 49.

FIG. 4 shows a schematic drawing of a hemodialysis clinic with six patients 10a-10f, each of which are wearing a body-worn monitor 51a-f and are connected to an individual hemodialysis machine 55a-f. Each body-worn monitor 51a-f communicates with a controller 22a-f in the hemodialysis machine through a cable 31a-f, and to the central monitoring station 77 through a wireless interface 75a-f. Alternatively, as described above, the cable 31a-f can be replaced with a wireless interface. Each hemodialysis machine 55a-f performs a hemodialysis process that typically last about 3-4 hours, and is typically performed 3 times each week. During treatment, the body-worn monitor continually sends vital sign and waveform information to the hemodialysis machine 55a-f and central monitoring station 77. Information affecting the performance of the hemodialysis machines 55a-f (e.g. the filtration rate and pump speed) can also be sent from the central monitoring station. In this way, a medical professional near the central monitoring station 77 can continuously monitor each patient 10a-f and their corresponding hemodialysis machine 55a-f from a single location, and adjust parameters on a particular hemodialysis machine when necessary.

Figure 5:
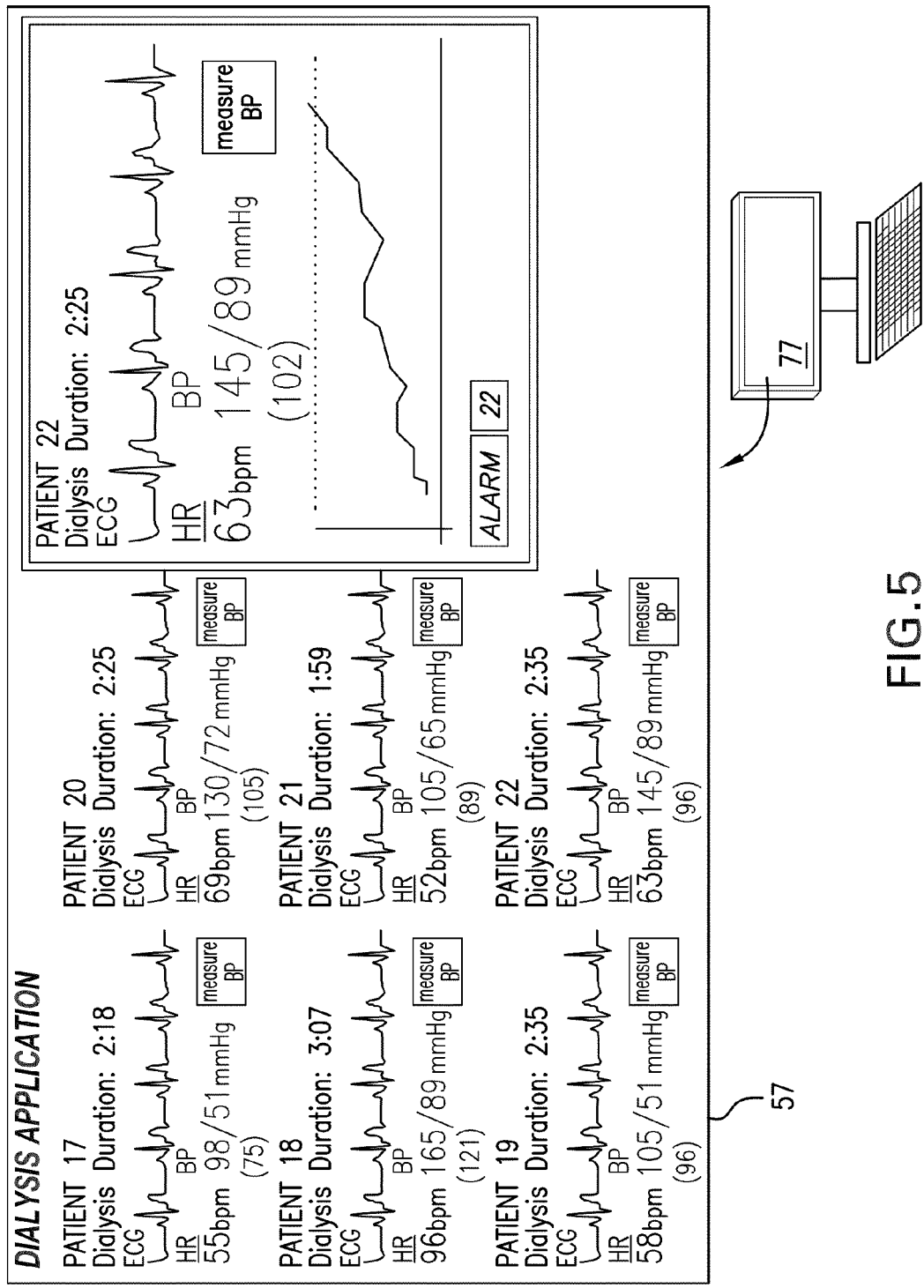
FIG. 5 shows a screen capture from a user interface operating on the central monitoring station of FIG. 4 that allows a healthcare professional to view information from multiple hemodialysis patients.

FIG. 5 shows a screen capture of the user interface 57 that operates on the central monitoring station 77 of FIG. 4. The user interface 57 displays each patient's vital signs information along with time-dependent ECG waveforms, patient information, and the duration of the hemodialysis process. Prior to each hemodialysis process, a medical professional can use the user interface 57 to set specific alarm thresholds for each patient, e.g. maximum and minimum values for a blood pressure value. Software associated with the user interface triggers an alarm if a vital sign exceeds a pre-set alarm threshold. In this case, the user interface 57 shows trending information describing the alarming vital sign, along with a window that highlights the patient information, vital signs, and time-dependent waveforms. This informs the medical professional that the specific patient is beginning to decompensate, thereby prompting them to adjust the hemodialysis process.

Figure 6:
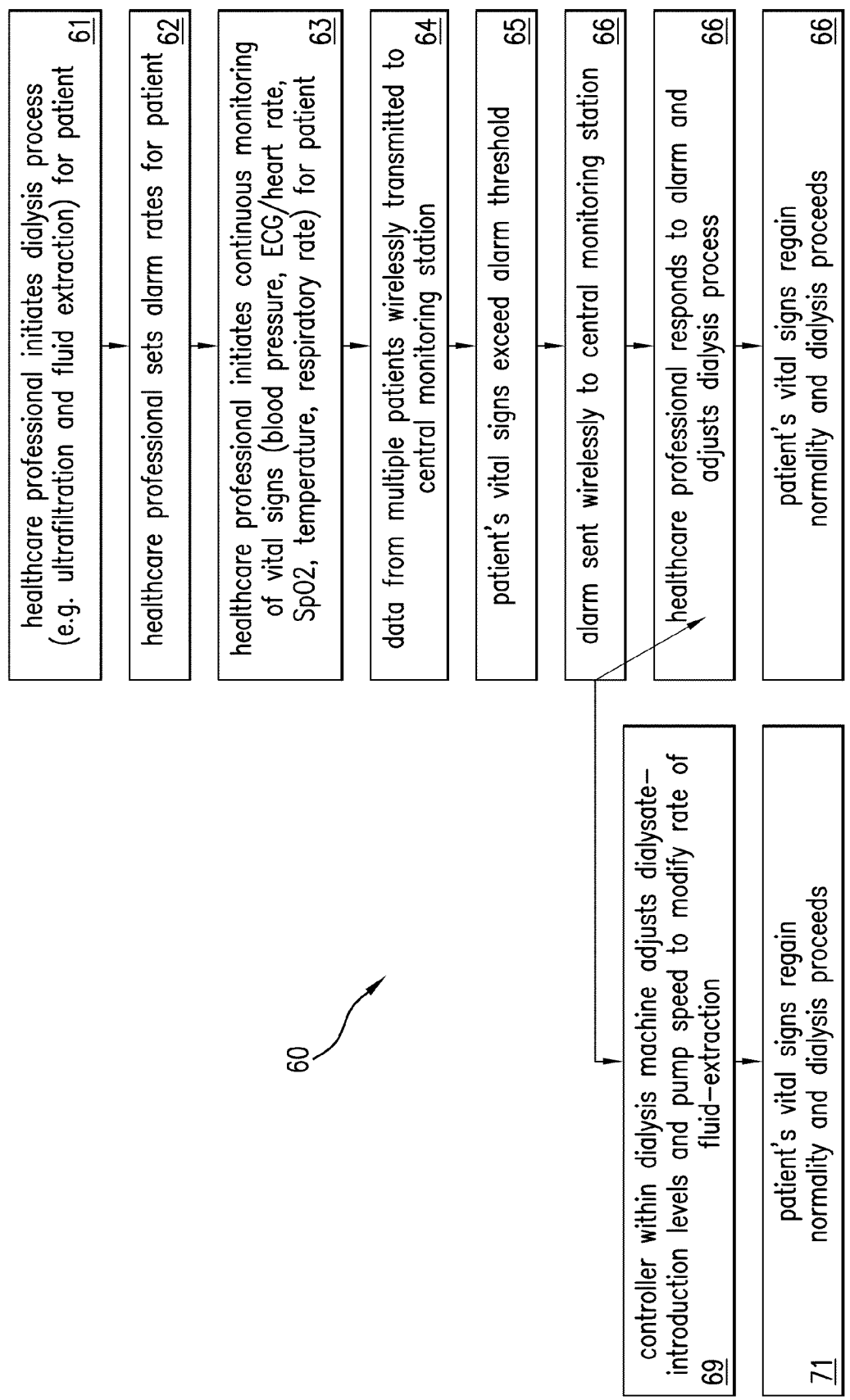
FIG. 6 shows a flow chart of an algorithm used in the system of FIG. 1 that allows a healthcare professional (Method A) or hemodialysis machine (Method B) to make a real-time correction in the hemodialysis process.

As shown in FIG. 6, the hemodialysis process can be adjusted manually by a medical professional (Method A), or automatically by the hemodialysis machine (Method B). In Method A, healthcare professional weighs the patient, inserts a needle in the dialysis access (i.e. fistula) to connect the patient to the hemodialysis machine, reviews the dialysis prescription and adjusts the settings/alarms on the hemodialysis machine accordingly (step 61). The first step of this process is for the medical professional to set alarm rates for patient (step 62) using the user interface shown in FIG. 5. Once this is done, the medical professional initiates continuous monitoring of vital signs (e.g. blood pressure, ECG/heart rate, SpO2, temperature, respiratory rate) for the patient (step 63) using the body-worn monitor. The monitor on each patient then wirelessly transmits information to the central monitoring station (step 64) so that the patient is continuously monitored. When a patient's vital signs exceed a predetermined threshold (step 65), an alarm is generated and sent wirelessly to central monitoring station (step 66). In response, a healthcare professional responds to alarm and adjusts parameters in the hemodialysis process (step 67), such as the ultrafiltration rate or the dialysate composition. A typical reason for hypertension and hypotension during hemodialysis is related to overly rapid changes in blood volume, with a drop in blood volume often resulting in hypotension, and an increase in blood volume often resulting in hypertension. Symptomatic hypotension, also known as intradialytic hypotension (IDH), as mentioned above, is one of the most common complications associated with hemodialysis, occurring in about 10-30% of patients. During IDH a patient's heart rate may increase to compensate for decreased blood flow in the body. The body-worn monitor can detect early changes in both blood pressure and heart rate as described above, and send them to the processing unit in the hemodialysis machine for analysis. Also affecting this analysis are parameters such as the patient's age, sex, weight, duration of the hemodialysis treatment, whether or not the patient is diabetic, and how long the patient has been receiving hemodialysis treatments. This information can be programmed into the body-worn monitor through its user interface. Once these and other data are processed, this step may result, for example, in the dialysis machine (or medical professional) decreasing the rate at which blood is extracted to counteract hypotension and an increase in heart rate. Alternatively, the machine (or medical professional) may increase the rate at which blood is extracted to counteract hypertension.

In yet another embodiment, the processing unit in the hemodialysis machine can counteract hypotension by increasing the level of sodium chloride in the dialysate. This measure can correct a physiological manifestation of an imbalance between the decrease in plasma volume during hemodialysis and a decrease in osmolality. These concepts are further described, for example, in the following reference, the contents of which are fully incorporated herein by reference: Kinet, J. et al.; Hemodynamic study of hypotension during hemodialysis; *Kidney International;* 21: 868-976 (1982).

After this adjustment period, the patient's hemodialysis process resumes (step 68). Alternatively, as shown by Method B, in response to an alarm, the controller within hemodialysis machine automatically adjusts the dialysate-introduction levels and rate of fluid extraction (step 69) as described above. If the process is correctly adjusted the patient's vital signs typically regain normality and hemodialysis continues (step 71). In other embodiments, software within the body-worn monitor can 'personalize' the response of the dialysis machine to patient-specific changes in blood pressure, heart rate, SpO2, and other information measured by the monitor (e.g. heart rate variability). For example, it can simultaneously monitor both the properties of the dialysis machine and the vital sign trends for a particular patient, and determine correlations between these two parameters. Algorithms operating on the monitor or dialysis machine can then estimate when life-threatening events, such as severe hypotension, are likely to occur during hemodialysis. The algorithm can then adjust hemodialysis to avoid these events.

FIGS. 7A-D, 8A-D, 9A-D show data from a formal feasibility study conducted on hemodialysis patients using the above-described Composite Method. The study was conducted at Fresenius Medical Clinic, located in San Diego, Calif., and monitored the accuracy of the Composite Method for both one-time and continuous measurements from patients with end-stage renal disease during 3-4 hour hemodialysis therapies. These patients provide a particularly challenging demographic for the Composite Method, as they tend to have stiff, inelastic arteries that often make it difficult to accurately perform even conventional blood pressure measurements. For the study, blood pressure was measured during eight separate 3-4 hour hemodialysis sessions conducted on five unique patients. A specialized blood pressure cuff, allowing simultaneous measurements using the composite, oscillometric (i.e. automated cuff), and auscultatory (i.e. manual cuff) methods, was used to measure all blood pressures. Measurements were made from the right arm of all but one patient, and both SYS and DIA were characterized. During the 3-4 hour hemodialysis period, blood pressure was measured with the Composite Method's pressure-free cNIBP measurement every 40 seconds. Using the specialized cuff, every 15 minutes both pressure-dependent and pressure-free measurements were made with the Composite Method, along with simultaneous measurements made using the oscillometric and auscultatory techniques. Both the pressure-dependent and pressure-free measurements made every 15 minutes were compared to those made by the oscillometric and auscultatory techniques to determine correlation. In addition, trends in the pressure-free measurements were compared to measurements made by the auscultatory technique to determine how well they predicted time-dependent blood pressure variations.

Figure 7A:
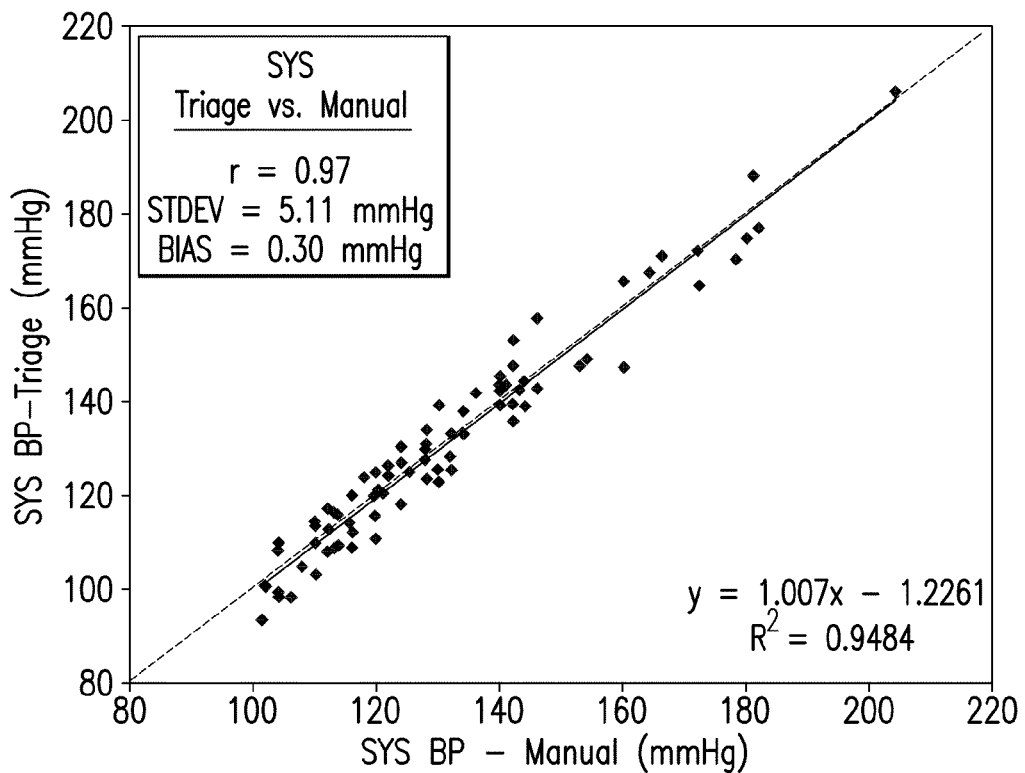
FIGS. 7A and 7B show, respectively, correlation graphs of SYS measured from hemodialysis patients with the pressure-dependent measurement of the Composite Method and a manual measurement, and SYS measured with an automatic measurement (e.g. oscillometry) and the manual measurement.
Figure 7B:
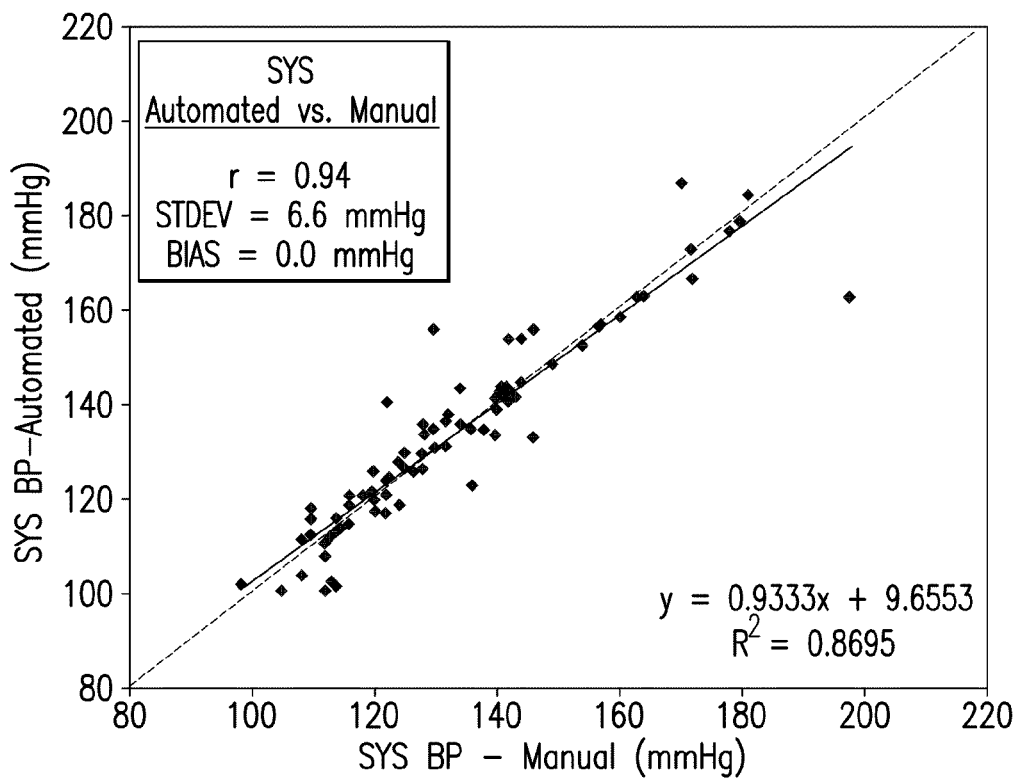
Figure 7C:
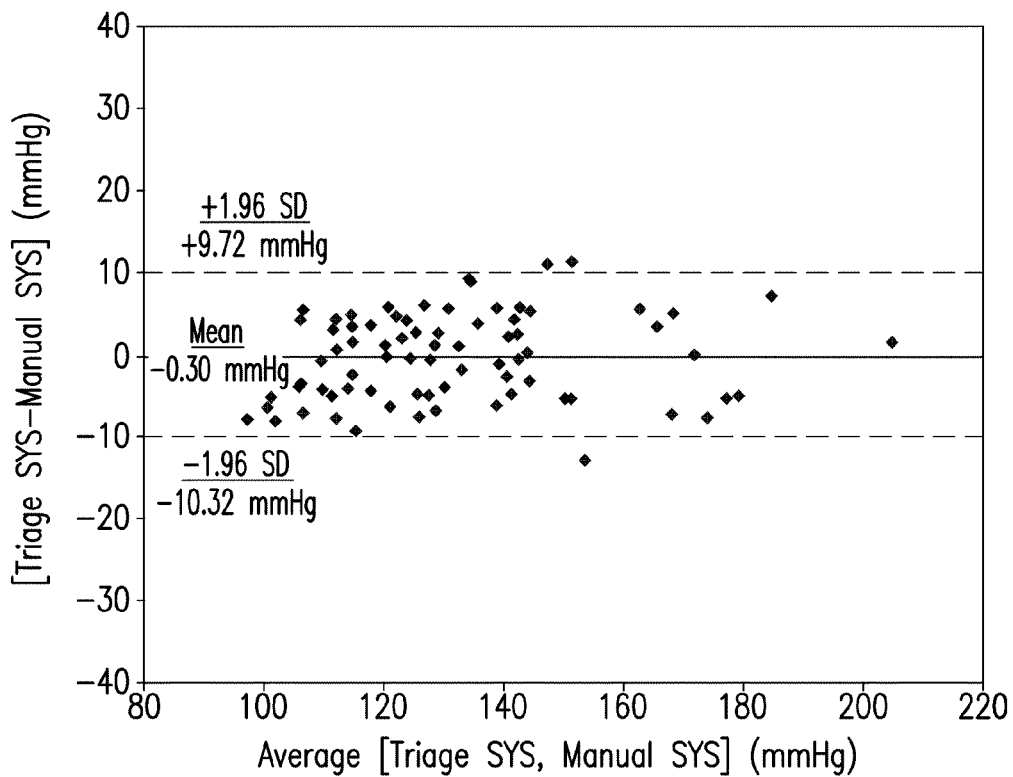
FIGS. 7C and 7D show Bland-Altman graphs generated from the data graphed in, respectively, FIGS. 7A and 7B.
Figure 7D:
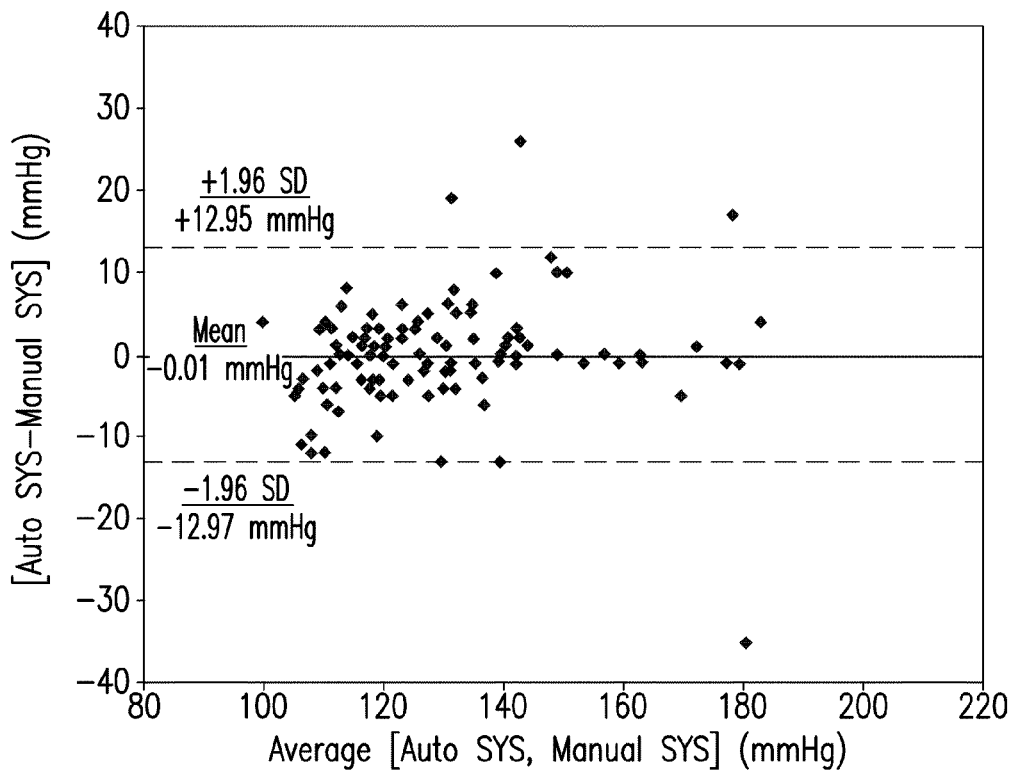
Figure 8A:
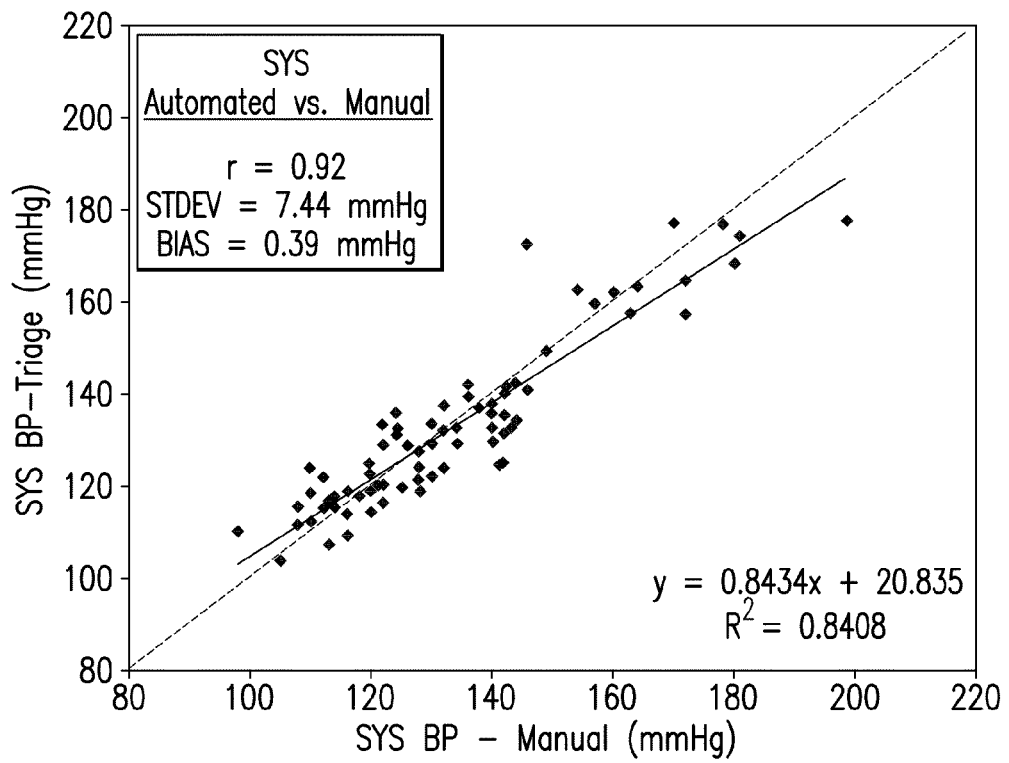
FIGS. 8A and 8B show, respectively, correlation graphs of SYS measured from hemodialysis patients with the pressure-free measurement of the Composite Method and a manual measurement, and SYS measured with an automatic measurement (e.g. oscillometry) and the manual measurement.
Figure 8B:
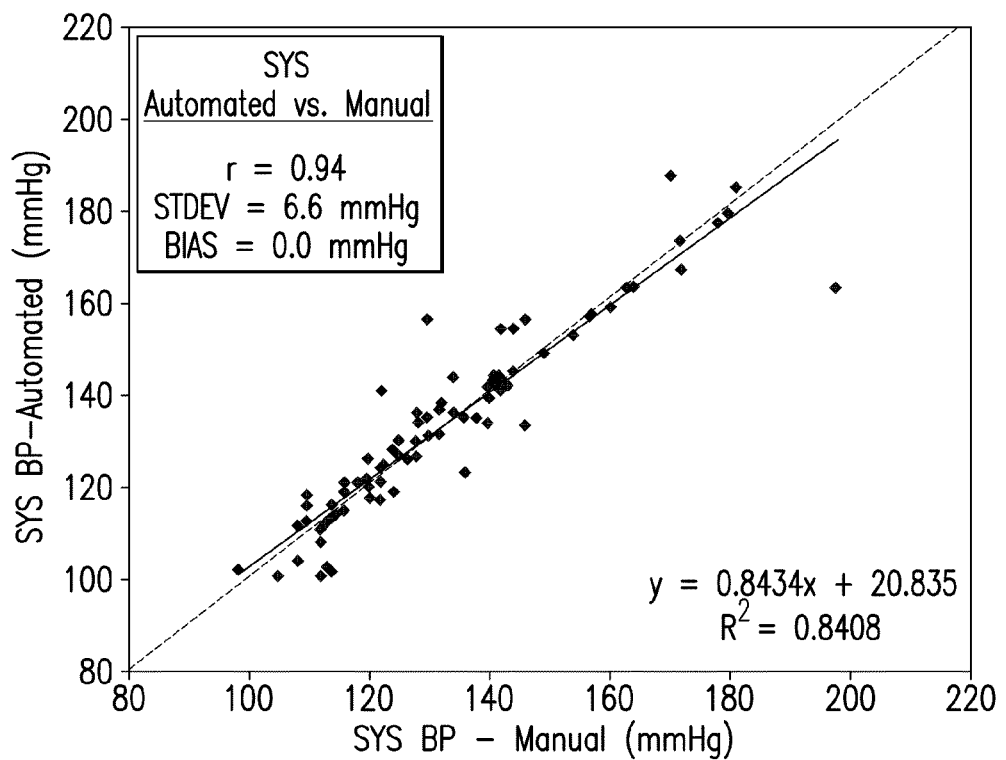
Figure 8C:
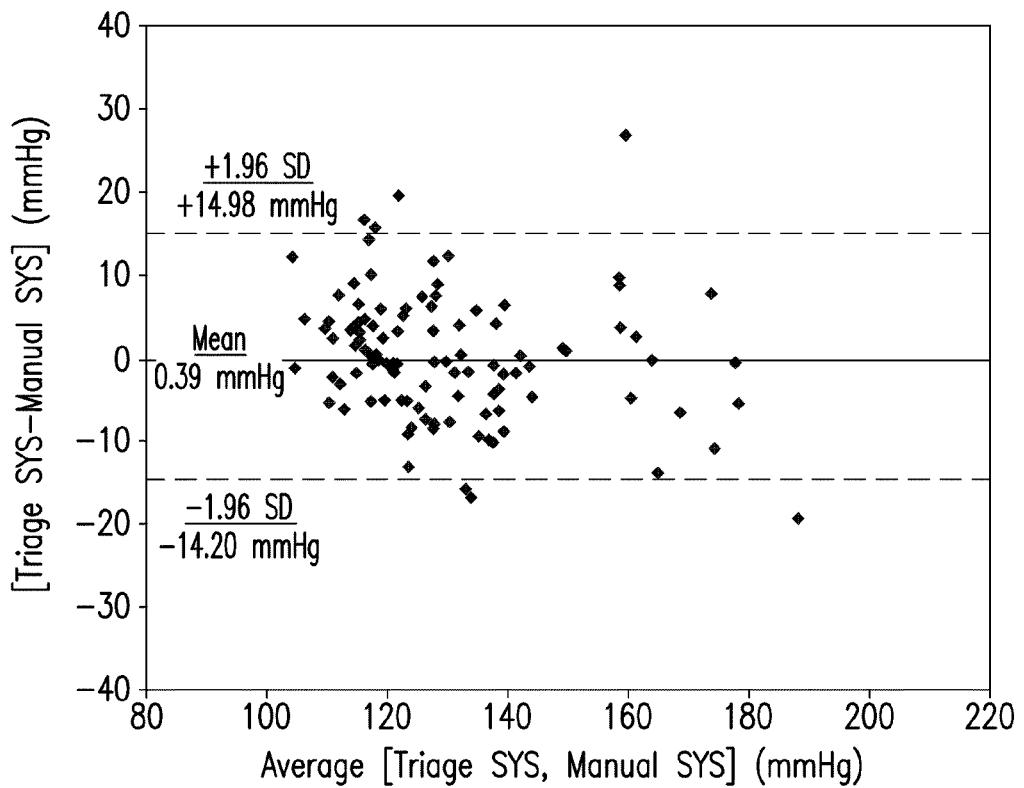
FIGS. 8C and 8D show Bland-Altman graphs generated from the data graphed in, respectively, FIGS. 8A and 8B.
Figure 8D:
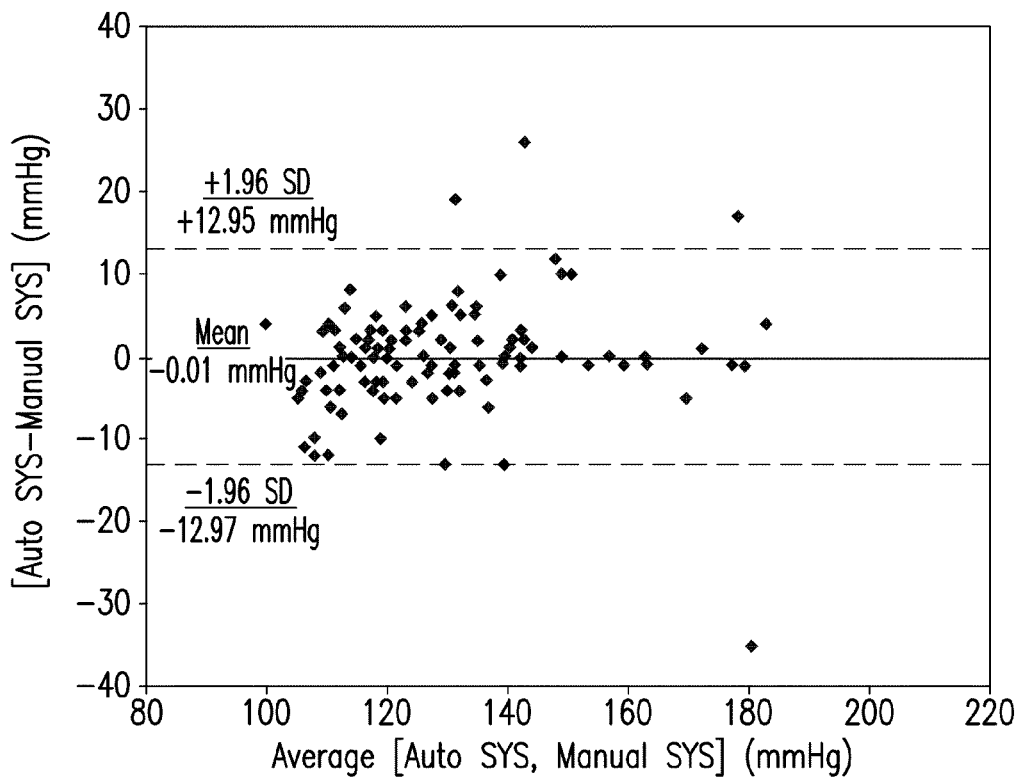
Figure 9A:
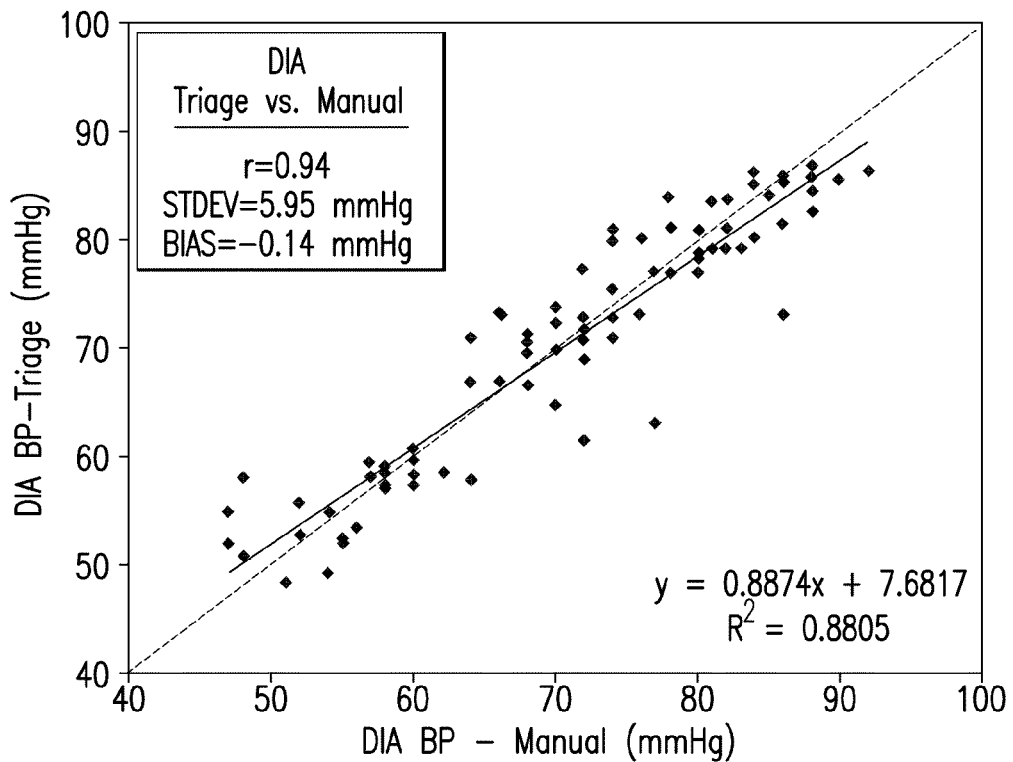
FIGS. 9A and 9B show, respectively, correlation graphs of DIA measured from hemodialysis patients with the pressure-free measurement of the Composite Method and a manual measurement, and DIA measured with an automatic measurement (e.g. oscillometry) and the manual measurement.
Figure 9B:
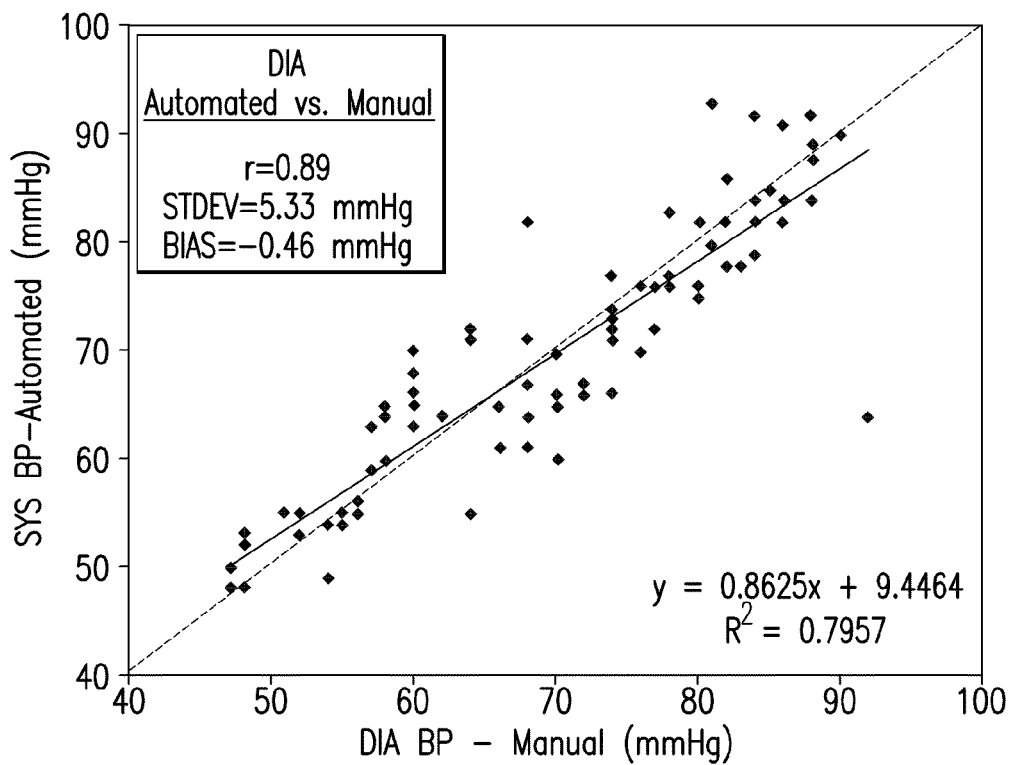
Figure 9C:
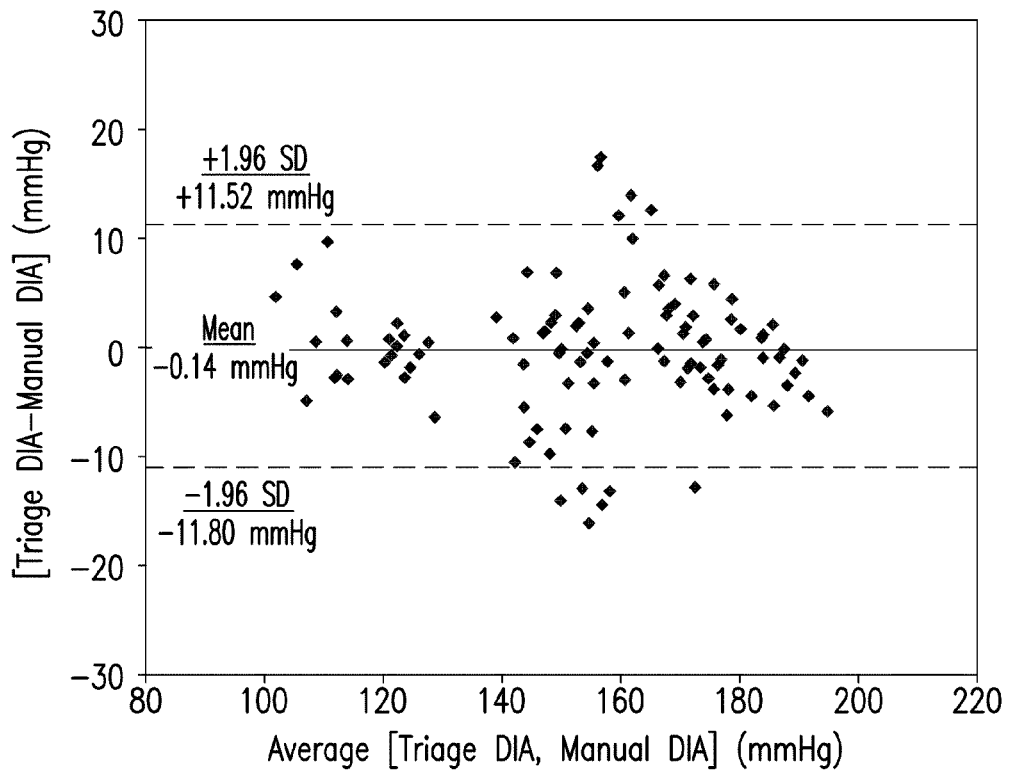
FIGS. 9C and 9D show Bland-Altman graphs generated from the data graphed in, respectively, FIGS. 9A and 9B.
Figure 9D:
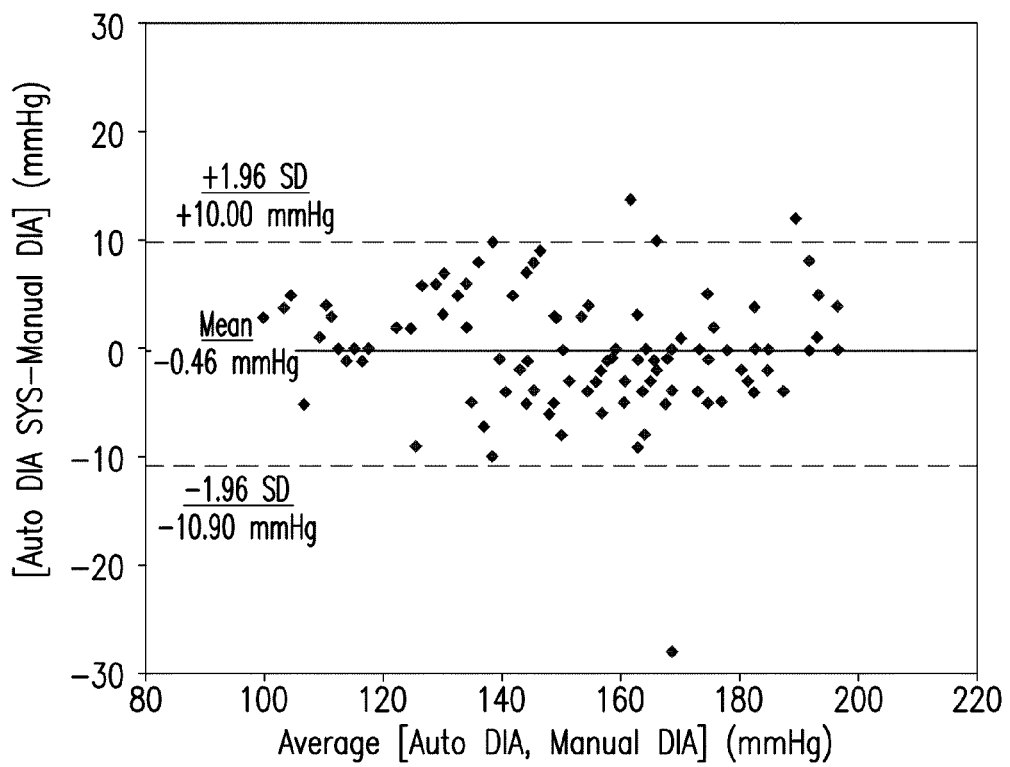

FIGS. 7A-D indicate the accuracy of the Composite Method's pressure-dependent measurement during hemodialysis. Data for these figures were determined during the 15-minute intervals where simultaneous auscultatory, oscillometric, and composite measurements were made. The first graph in FIG. 7A shows the correlation between SYS measured with the pressure-dependent measurement of the composite measurement (y-axis) and the auscultatory technique (x-axis). FIG. 7B shows correlation between SYS measured with the oscillometric technique (y-axis) and the auscultatory technique (x-axis). The correlation between the composite and auscultatory techniques (r=0.97) indicates the accuracy of this measurement, as does the bias of (−0.3 mmHg) and standard deviation (5.1 mmHg). The best-fit slope of the correlation was 1.00, which is identical to within experimental error to the ideal slope of 1. The correlation and standard deviation between the auscultatory and oscillometric techniques were similar (r=0.94, SD=±6.6 mmHg), while the bias was slightly better (0.0 mmHg) than the data from the Composite Method, and the slope slightly deviated (0.93) from the ideal slope of 1. The Bland-Altman plots shown in FIG. 7C indicate no systematic error is present in the Composite Method.

FIGS. 8A-D and 9A-D show how the Composite Method's pressure-free measurements compared to measurements made with the auscultatory and oscillometric techniques for both SYS and DIA. In this case, pressure-free measurements were determined a few seconds before the comparative measurements. In general, the agreements between the pressure-free and auscultatory measurements for SYS (FIGS. 8A and 8C; r=0.92; standard deviation=7.4 mmHg; bias=0.4 mmHg) and DIA (FIGS. 9A and 9C; r=0.94; standard deviation=5.95 mmHg; bias=−0.1 mmHg) were slightly worse than those for the pressure-dependent measurements, but still well within the AAMI/ANSI SP:10 guidelines mandated by the FDA (SD<8 mmHg; BIAS<|+/−5 mmHg|) for 510(k) approval. Errors are likely partially due to the fact that these measurements, unlike the pressure-dependent measurements, are made indirectly from different heart beats detected from the patient. Beat-to-beat variations in blood pressure, as well hemodynamic components unaffected by blood pressure but present in the pressure-free signal, likely contribute to this error.

FIGS. 10A and 10B show how the body-worn monitor 51 described with respect to FIG. 1 attaches to a patient 10. These figures show two configurations of the system: FIG. 10A shows the system used during the indexing portion of the Composite Method, and includes a pneumatic, cuff-based system 85, while FIG. 10B shows the system used for subsequent continuous monitoring of the patient featuring a cNIBP measurement. The indexing measurement, as described above, typically takes about 40 seconds, and is typically performed once every 4 hours. Once the indexing measurement is complete the cuff-based system is typically removed from the patient. The remainder of the time the body-worn monitor 51 performs the cNIBP measurement.

Figure 11:
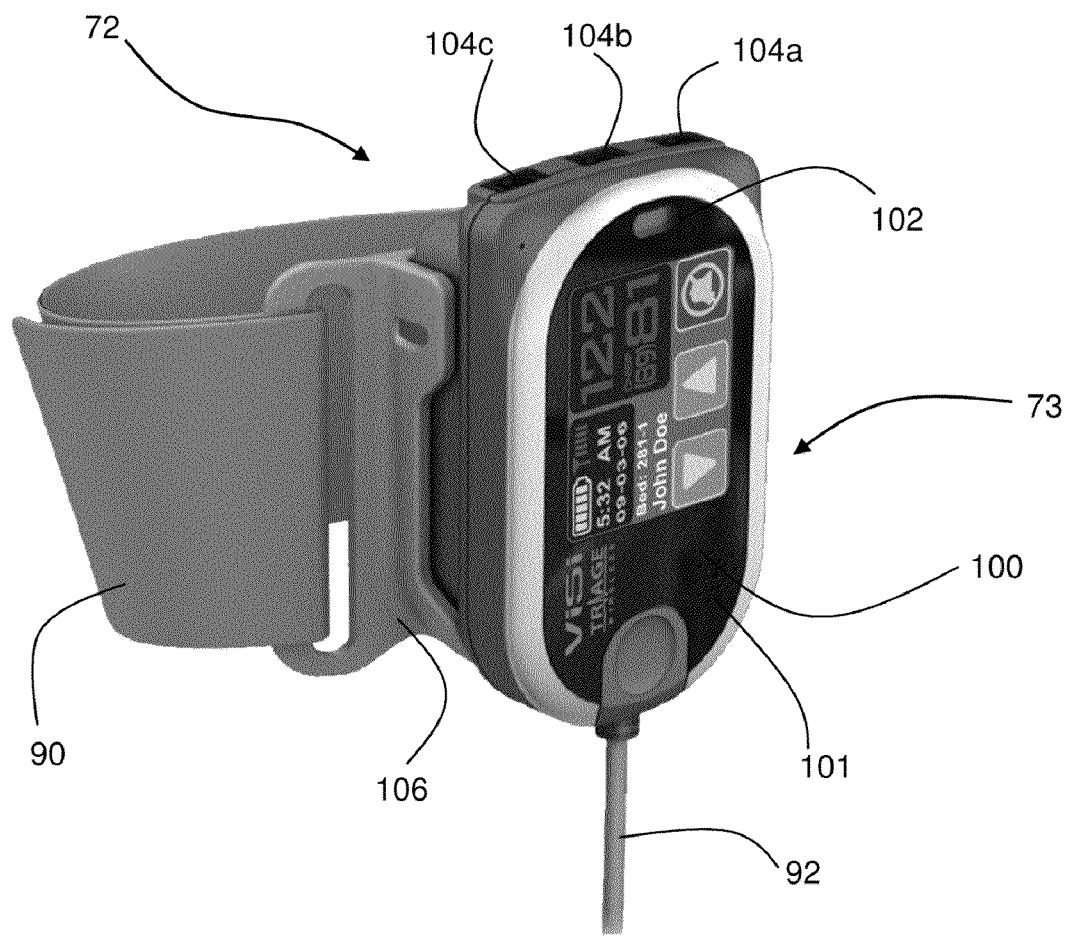
FIG. 11 shows an image of the wrist-worn transceiver featured in the body-worn monitor of FIGS. 10A and 10B.

The body-worn monitor 51 features a wrist-worn transceiver 72, described in more detail in FIG. 11, featuring a touch panel interface 73 that displays blood pressure values and other vital signs. A wrist strap 90 affixes the transceiver 72 to the patient's wrist like a conventional wristwatch. A cable 92 connects an optical finger sensor 94 that wraps around the base of the patient's thumb to the transceiver 72. During a measurement, the finger sensor 94 generates a time-dependent PPG which is processed along with an ECG to measure blood pressure. PTT-based measurements made from the thumb yield excellent correlation to blood pressure measured with a femoral arterial line; this provides an accurate representation of blood pressure in the central regions of the patient's body.

To determine waveforms indicating patient motion, the body-worn monitor 51 features 3 separate accelerometers located at different portions on the patient's arm. The first accelerometer is surface-mounted on a circuit board in the wrist-worn transceiver 72 and measures signals associated with movement of the patient's wrist. The second accelerometer is included in a small bulkhead portion 96 included along the span of the cable 82. During a measurement, a small piece of disposable tape, similar in size to a conventional bandaid, affixes the bulkhead portion 96 to the patient's arm. In this way the bulkhead portion 96 serves two purposes: 1) it measures a time-dependent motion waveform from the mid-portion of the patient's arm, thereby allowing their posture and arm height to be determined as described in detail below; and 2) it secures the cable 82 to the patient's arm to increase comfort and performance of the body-worn monitor 51.

The cuff-based module 85 features a pneumatic system 76 that includes a pump, valve, pressure fittings, pressure sensor, analog-to-digital converter, microcontroller, and rechargeable battery. During an indexing measurement, it inflates a disposable cuff 84 and performs two measurements according to the composite technique: 1) an inflation-based measurement of oscillometry to determine values for SYS, DIA, and MAP; and 2) it determines a patient-specific relationship between PTT and MAP.

The cuff 84 within the cuff-based pneumatic system 85 is typically disposable and features an internal, airtight bladder that wraps around the patient's bicep to deliver a uniform pressure field. During the indexing measurement, pressure values are digitized by the internal analog-to-digital converter, and sent through a cable 86, along with SYS, DIA, and MAP blood pressures, to the wrist-worn transceiver 72 for processing as described above. Once the cuff-based measurement is complete, the cuff-based module 85 is removed from the patient's arm and the cable 86 is disconnected from the wrist-worn transceiver 72. cNIBP is then determined using PTT, as described in detail above.

To determine an ECG, the body-worn monitor 51 features a small-scale, three-lead ECG circuit integrated directly into a bulkhead 74 that terminates the ECG cable 82. The ECG circuit features an integrated circuit that collects electrical signals from three chest-worn ECG electrodes 78a-c connected through cables 80a-c. As described above, one of the ECG electrodes can be included in the sensor 94 worn on the patient's finger. Alternatively, the ECG electrodes 78a-c are disposed in a conventional 'Einthoven's Triangle' configuration which is a triangle-like orientation of the electrodes 78a-c on the patient's chest that features 3 unique ECG vectors. From these electrical signals the ECG circuit determines up to three ECG waveforms, which are digitized and sent through a cable 82 to the wrist-worn transceiver 72. In a preferred embodiment, the ECG waveforms and other information generated by sensors within the body-worn monitor 51 are sent to the wrist-worn transceiver 72 according to a serial protocol. A preferred serial communication protocol is the 'controlled area network' (CAN) protocol, which is often used to connect electrical systems used in automobiles. ECG data sent to the transceiver 72 is processed with the PPG to determine the patient's blood pressure. Heart rate and respiratory rate are determined directly from the ECG waveform using known algorithms. The cable bulkhead 74 also includes an accelerometer that measures motion associated with the patient's chest, as described above. This can be used to determine the patient's posture, activity level, and degree of motion, as described in the above-referenced patent applications, the contents of which have been previously incorporated by reference. More sophisticated ECG circuits can plug into the wrist-worn transceiver to replace the three-lead system shown in FIGS. 10A and 10B. These ECG circuits can include, e.g., five and twelve leads.

FIG. 11 shows a close-up view of the wrist-worn transceiver 72. As described above, it attaches to the patient's wrist using a flexible strap 90 which threads through two D-ring openings in a plastic housing 106. The transceiver 72 features a touchpanel display 100 that renders a graphical user interface 73 which is altered depending on the viewer (typically the patient or a medical professional). Specifically, the transceiver 72 includes a small-scale infrared barcode scanner 102 that, during use, can scan a barcode worn on a badge of a medical professional. The barcode indicates to the transceiver's software that, for example, a nurse or doctor is viewing the user interface. In response, the user interface 73 displays vital sign data and other medical diagnostic information appropriate for medical professionals. Using this interface 73, the nurse or doctor, for example, can view the vital sign information, set alarm parameters, and enter information about the patient (e.g. their demographic information, medication, or medical condition). The nurse can press a button on the user interface 73 indicating that these operations are complete. At this point, the display 100 renders an interface that is more appropriate to the patient, e.g. it displays parameters similar to those from a conventional wristwatch, such as time of day and battery power.

The transceiver 72 features three connectors 104a-c on the side of its upper portion, each which supports CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 104a-c, and means that these connectors are not associated with a specific cable. Any cable connecting to the transceiver can be plugged into any connector 104a-c. The first connector 104a receives the cable 82 that transports a digitized ECG waveform determined from the ECG circuit and electrodes, and digitized motion waveforms measured by accelerometers in the cable bulkhead 74 and the bulkhead portion 96 associated with the ECG cable 82. The second CAN connector 104b receives the cable 86 that connects to the cuff-based system 85 and is used for the pressure-dependent indexing measurement. This connector 104b is used to receive a time-dependent pressure waveform delivered by the pneumatic system 85 to the patient's arm, along with values for SYS, DIA, and MAP values determined during the indexing measurement. The cable 86 is unplugged from the connector 104b once the indexing measurement is complete, and is plugged back in after approximately 4 hours for another indexing measurement.

The final CAN connector 104c can be used for an ancillary device, e.g. a glucometer, infusion pump, body-worn insulin pump, ventilator, or end-tidal $CO_2$ delivery system. As described above, digital information generated by these systems will include a header that indicates their origin so that the CPU can process them accordingly.

The transceiver includes a speaker 102 that allows a medical professional to communicate with the patient using a voice over Internet protocol (VOIP). For example, using the speaker 102 the medical professional could query the patient from a central nursing station or mobile phone connected to a wireless, Internet-based network within the dialysis clinic. Or the medical professional could wear a separate transceiver similar to the shown in FIG. 11, and use this as a communication device. In this application, the transceiver 72 worn by the patient functions much like a conventional cellular telephone or 'walkie talkie': it can be used for voice communications with the medical professional and can additionally relay information describing the patient's vital signs and motion.

Figure 12:
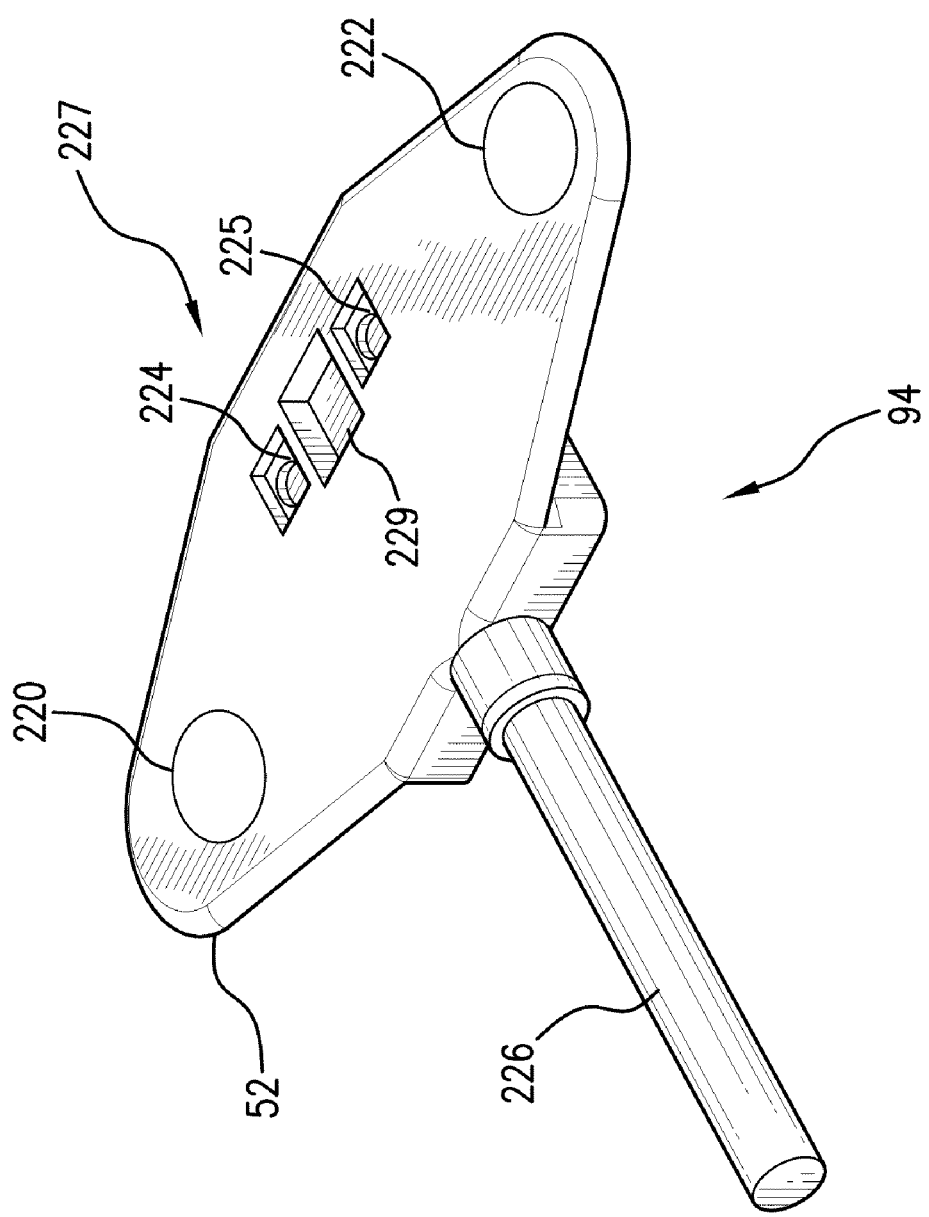
FIG. 12 is a three-dimensional plan view of a finger-worn sensor that connects to the wrist-worn transceiver of FIG. 11 and includes both an optical sensor and two electrodes.

FIG. 12 shows an end portion 52 of a finger sensor 94 that connects to the body-worn monitor described above. The sensor 94 features an optical sensor 227 and two electrodes 220, 222 for measuring optical and electrical signals from the patient. It is designed for easy application during a hemodialysis process, and because of the two electrodes 220, 222 can minimize the number of additional electrodes that need to be applied to the patient's chest. The optical sensor 227 includes two LEDs 224, 225 which can operate in either a transmission or reflection mode geometry, and a photodetector 229. For reflection-mode measurements, the LEDs 224, 225 radiate near 570 nm, and are located adjacent to the photodetector 229. For transmission-mode measurements, one LED 224 typically operates near 900 nm, while the second LED 225 typically operates near 600 nm. In this case the photodetector 229 is spaced from both LEDs so that in can detect radiation that propagates through the patient's finger. Additionally, having LEDs at these wavelengths allows for pulse oximetry measurements, described above with the referenced patent applications. Two metal electrodes 220 and 222 are positioned on either side of the optical sensor 227. One of these electrodes 200 serves as a ground, while the other 222 generates an electrical signal that generates an ECG when processed with a similar signal from an electrode of the patient's chest. Both the electrical and optical signals travel through a cable 226 that attaches to the body-worn monitor as described above.

In addition to the methods described above, a number of additional methods can be used to calculate blood pressure from the PPG and ECG waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) CUFFLESS BLOOD PRESSURE MONITOR AND ACCOMPANYING WIRELESS MOBILE DEVICE (U.S. Ser. No. 10/967,511; filed Oct. 18, 2004); 5) BLOOD PRESSURE MONITORING DEVICE FEATURING A CALIBRATION-BASED ANALYSIS (U.S. Ser. No. 10/967,610; filed Oct. 18, 2004); 76) PERSONAL COMPUTER-BASED VITAL SIGN MONITOR (U.S. Ser. No. 10/906,342; filed Feb. 15, 2005); 87) PATCH SENSOR FOR MEASURING BLOOD PRESSURE WITHOUT A CUFF (U.S. Ser. No. 10/906,315; filed Feb. 14, 2005); 8) PATCH SENSOR FOR MEASURING VITAL SIGNS (U.S. Ser. No. 11/160,957; filed Jul. 18, 2005); 9) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 10) HAND-HELD MONITOR FOR MEASURING VITAL SIGNS (U.S. Ser. No. 11/162,742; filed Sep. 21, 2005); 11) CHEST STRAP FOR MEASURING VITAL SIGNS (U.S. Ser. No. 11/306,243; filed Dec. 20, 2005); 12) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 13) BILATERAL DEVICE, SYSTEM AND METHOD FOR MONITORING VITAL SIGNS (U.S. Ser. No. 11/420,281; filed May 25, 2006); 14) SYSTEM FOR MEASURING VITAL SIGNS USING BILATERAL PULSE TRANSIT TIME (U.S. Ser. No. 11/420,652; filed May 26, 2006); 15) BLOOD PRESSURE MONITOR (U.S. Ser. No. 11/530,076; filed Sep. 8, 2006); 16) TWO-PART PATCH SENSOR FOR MONITORING VITAL SIGNS (U.S. Ser. No. 11/558,538; filed Nov. 10, 2006); 17) MONITOR FOR MEASURING VITAL SIGNS AND RENDERING VIDEO IMAGES (U.S. Ser. No. 11/682,177; filed Mar. 5, 2007); 18) DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); 19) VITAL SIGN MONITOR MEASURING BLOOD PRESSURE USING OPTICAL, ELECTRICAL, AND PRESSURE WAVEFORMS (U.S. Ser. No. 12/138,194; filed Jun. 12, 2008); and, 20) VITAL SIGN MONITOR FOR CUFFLESSLY MEASURING BLOOD PRESSURE CORRECTED FOR VASCULAR INDEX (U.S. Ser. No. 12/138,199; filed Jun. 12, 2008).

In other embodiments, the body-worn monitor shown in FIGS. 10A and 10B can be worn by a hemodialysis patient outside of a dialysis clinic and in between hemodialysis treatments. For example, the monitor could continually measure and record vital signs and waveforms from the patient during normal day-to-day activities, such as work and sleep. Such monitoring serves two primary functions. First, it allows real-time detection of life-threatening cardiac events (e.g. bradycardia, bradytachycardia, asystole, ventricular fibrillation, ventricular tachycardia, and apnea) which are common in hemodialysis patients, and can lead to serious injury and sudden death between hemodialysis treatments. With the body-worn monitor, each of these cardiac events can be detected within seconds of occurring through analysis of the above-described electrical waveform used to measure blood pressure (shown as 18 in FIG. 2). Second, analysis of trends in the electrical waveform, such as a gradual change in heart rate, heart rate variability, or shape of the various ECG components (e.g. QRS complex, T-wave), taken alone or combined with trends for other vital signs, may provide information that can help predict a cardiac event before it actually occurs. Or alternatively this information may be collected and analyzed to adjust follow-on hemodialysis processes.

In embodiments, a hemodialysis patient would wear the body-worn monitor during a hemodialysis treatment. During this period the monitor wirelessly transmits blood pressure and heart rate values to both the hemodialysis machine and the display at the central station using a short-range wireless system, such as those based on 802.11 or 802.16.4. After the treatment, the patient would continue to wear the monitor, which would be adjusted (through, e.g., a setting on its user interface) to operate in a mode outside of the dialysis clinic. In this mode, for example, the monitor could transmit data through a long-range wireless system, such as a cellular system, or through an Internet-based system. A cellular modem operating in this mode could attach to the wrist-worn transceiver through one of the CAN connectors (104a-c in FIG. 11) located on its side portion; these connectors, as described above, operate a serial communication protocol to communicate with the cellular modem. The transmitter sends information from the patient to an Internet-based system, which can then be viewed by a medical professional to remotely monitor the patient. During this monitoring an ambulance could be dispatched to the patient if a cardiac event were to occur.

In still other embodiments, the central monitoring station stores and analyses vital signs, trends, and properties measured from the vital signs (e.g. heart rate variability) that are continuously monitored during the hemodialysis process to identify patients that may be at risk outside of the clinic. These patients are then flagged for associated pre-emptive treatments. In this embodiment, for example, the central monitoring station may generate a printout of information and associated reports collected during previous dialysis treatments that the patient can then bring to the pre-emptive treatment.

Still other embodiments are within the scope of the following claims.

What is claimed is:

1. A system for characterizing a patient comprising:
a vital sign monitor, attached to the patient and configured to interface to a hemodialysis machine, comprising:
a sensor configured to be worn on the patient's finger, the sensor comprising an optical sensor comprising a light source and a photodetector for measuring an optical waveform from the patient;
a first electrode, configured to be worn on the patient's body and to measure a first electrical signal from the patient;
a second electrode, configured to be worn on the patient's body and to measure a second electrical signal from the patient;
an electrical circuit configured to receive the first and second electrical signals and amplify and process them to generate an electrical waveform;
a processing module configured to process: i) the optical waveform and the electrical waveform to determine a time difference between features in these waveforms; and ii) a blood pressure calibration and the time difference to determine a blood pressure value;
a first transmission system for transmitting blood pressure values to the hemodialysis machine when the patient is connected to the hemodialysis machine; and
a second transmission system for transmitting information to a remote receiver when the patient is disconnected from the hemodialysis machine.

2. The system of claim 1, wherein the second transmission system comprises a wireless transmission system.

3. The system of claim 1, wherein the remote receiver is a computer.

4. The system of claim 3, wherein the computer is configured to be connected to the Internet.

5. The system of claim 4, wherein the computer is configured to be connected to a call center.

6. The system of claim 1, wherein the vital sign monitor further comprises an input port configured to connect to the second transmission system.

7. The system of claim 1, wherein the first and second transmission systems are comprised by a common transmission system.

8. The system of claim 7, wherein the first transmission system comprises compiled computer code configured to instruct the first transmission system to transmit blood pressure values to the hemodialysis machine, and the second transmission system comprises compiled computer code configured to instruct the second transmission system to transmit information to the remote receiver.

9. The system of claim 1, wherein the second transmission system is further configured to transmit a blood pressure value to the remote receiver.

10. The system of claim 1, wherein the processing module is further configured to process the electrical waveform to determine a heart rate value.

11. The system of claim 10, wherein the second transmission system is further configured to transmit the heart rate value to the remote receiver.

12. The system of claim 1, wherein the electrical waveform is an ECG waveform.

13. The system of claim 12, wherein the processing module is further configured to process the ECG waveform to determine a cardiac parameter.

14. The system of claim 13, wherein the cardiac parameter is selected from the group comprising parameters describing one of high heart rate, low heart rate, bradycardia, bradytachycardia, asystole, ventricular fibrillation, ventricular tachycardia, apnea, and heart rate variability.

15. The system of claim 14, wherein the processing module is further configured to process the cardiac parameter to determine an alarm.

16. The system of claim 15, wherein the second transmission system is further configured to transmit the alarm to the remote receiver.

17. The system of claim 12, wherein the second transmission system is further configured to transmit the ECG waveform to the remote receiver.

18. The system of claim 1, wherein the vital sign monitor further comprises a user interface.

19. The system of claim 18, wherein the user interface is configured to activate the first transmission system and the second transmission system.

20. The system of claim 1, wherein the vital sign monitor further comprises an input port, and the sensor comprises a cable configured to plug into the input port so that the processing module can receive information from the sensor.

* * * * *